(12) United States Patent
Centen

(10) Patent No.: US 12,083,068 B2
(45) Date of Patent: Sep. 10, 2024

(54) MEASUREMENT OF A COMPRESSION PARAMETER FOR CPR ON A SURFACE

(71) Applicant: Physio-Control Canada Sales Ltd., Mississauga (CA)

(72) Inventor: Corey Centen, Toronto (CA)

(73) Assignee: PHYSIO-CONTROL, INC., Redmond, WA (US)

( * ) Notice: Subject to any disclaimer, the term of this patent is extended or adjusted under 35 U.S.C. 154(b) by 316 days.

(21) Appl. No.: 17/191,471

(22) Filed: Mar. 3, 2021

(65) Prior Publication Data
US 2022/0304889 A1  Sep. 29, 2022

Related U.S. Application Data

(63) Continuation of application No. 14/501,354, filed on Sep. 30, 2014, now abandoned, which is a (Continued)

(51) Int. Cl.
*A61H 31/00* (2006.01)
*A61N 1/04* (2006.01)
*A61N 1/39* (2006.01)

(52) U.S. Cl.
CPC ............ *A61H 31/00* (2013.01); *A61H 31/004* (2013.01); *A61H 31/007* (2013.01);
(Continued)

(58) Field of Classification Search
CPC .............. A61H 31/004; A61H 2201/10; A61H 2201/1635; A61H 2201/5043;
(Continued)

(56) References Cited

U.S. PATENT DOCUMENTS 4,314,251 A   2/1982   Raab
6,062,216 A   5/2000   Corn
(Continued)

FOREIGN PATENT DOCUMENTS

EP   1350466 A1   10/2003
EP   1491175 A1   12/2004
(Continued)

OTHER PUBLICATIONS

International Search Report for International Application No. PCT/CA2010/000330, dated Jul. 2, 2010, 4 pages.
(Continued)

*Primary Examiner* — Rachel T Sippel
(74) *Attorney, Agent, or Firm* — Miller Nash LLP

(57) ABSTRACT

A device for the determination of at least one compression parameter during the administration of cardiopulmonary resuscitation (CPR) on a patient. The device includes a compression unit adapted to move in accordance with the chest of a patient and a surface unit adapted to move in accordance with a surface supporting the patient. The compression unit has one of a signal component and reference component, the surface unit has the other of the signal component and the reference component. The device also includes a processor configured to determine a relative measurement between the compression unit and the surface unit using data derived from the signal component and the reference component. The processor is further configured to determine the at least one compression parameter based on the relative measurement. The determined at least one compression parameter takes into account any motion and/or displacement of the surface.

18 Claims, 41 Drawing Sheets

Related U.S. Application Data continuation of application No. 12/579,455, filed on Oct. 15, 2009, now Pat. No. 8,876,742.

(60) Provisional application No. 61/235,584, filed on Aug. 20, 2009, provisional application No. 61/158,002, filed on Mar. 6, 2009.

(52) U.S. Cl.
CPC ........... *A61H 31/008* (2013.01); *A61N 1/046* (2013.01); *A61N 1/0492* (2013.01); *A61N 1/39044* (2017.08); *A61H 31/005* (2013.01); *A61H 2201/10* (2013.01); *A61H 2201/1635* (2013.01); *A61H 2201/5043* (2013.01); *A61H 2201/5061* (2013.01); *A61H 2201/5064* (2013.01); *A61H 2201/5071* (2013.01); *A61H 2201/5084* (2013.01); *A61H 2205/084* (2013.01); *A61H 2230/065* (2013.01)

(58) Field of Classification Search
CPC .... A61H 2201/5064; A61H 2201/5071; A61H 2201/5084; A61H 2205/084; A61H 2230/065; A61H 31/00–005; A61H 31/007–008; A61H 2201/5061–5066; A61H 2201/5085; A61N 1/046; A61N 1/0492; A61N 1/39044
See application file for complete search history.

(56) References Cited

U.S. PATENT DOCUMENTS

| | | | |
|---|---|---|---|
| 6,306,107 B1* | 10/2001 | Myklebust | A61H 31/007 600/595 |
| 6,323,942 B1 | 11/2001 | Bamji | |
| 7,402,996 B2 | 7/2008 | Arai et al. | |
| 2002/0026229 A1* | 2/2002 | Weil | A61N 1/14 607/142 |
| 2002/0055694 A1 | 5/2002 | Halperin et al. | |
| 2004/0082888 A1 | 4/2004 | Palazzolo et al. | |
| 2004/0210171 A1* | 10/2004 | Palazzolo | A61B 5/053 601/41 |
| 2004/0267325 A1 | 12/2004 | Geheb et al. | |
| 2005/0101889 A1 | 5/2005 | Freeman et al. | |
| 2005/0131465 A1* | 6/2005 | Freeman | A61N 1/3993 607/5 |
| 2005/0217675 A1* | 10/2005 | Thompson | A61M 16/0078 128/202.28 |
| 2006/0247560 A1 | 11/2006 | Halperin et al. | |
| 2007/0252586 A1 | 11/2007 | Arai et al. | |
| 2007/0276300 A1 | 11/2007 | Olson et al. | |
| 2008/0145827 A1 | 6/2008 | Strand et al. | |
| 2008/0146973 A1 | 6/2008 | Lund et al. | |
| 2008/0171311 A1 | 7/2008 | Centen et al. | |
| 2008/0300517 A1 | 12/2008 | Nysaether | |
| 2008/0312565 A1 | 12/2008 | Celik-Butler et al. | |
| 2010/0022904 A1 | 1/2010 | Centen | |

FOREIGN PATENT DOCUMENTS

| | | |
|---|---|---|
| EP | 1491176 A1 | 12/2004 |
| EP | 1645841 A1 | 4/2006 |
| EP | 1859770 A1 | 11/2007 |
| WO | 2003101537 A1 | 12/2003 |
| WO | 2004073797 A1 | 9/2004 |
| WO | 2010009531 A1 | 1/2010 |
| WO | 2010099628 A1 | 9/2010 |

OTHER PUBLICATIONS

Perkins et al., "Compression feedback devices over estimate chest compression depth when performed on a bed," Resuscitation, Jan. 2009; 80(1); 79-82, Epub Oct. 25, 2008.

Van Berkom et al., "Does use of the CPREzy involve more work than CPR without feedback?" Resuscitation, Jul. 2008; 78(a): 66-70. Epub Apr. 18, 2008.

International Search Report for International Application No. PCT/CA2009/001475, dated Jan. 12, 2010, 5 pages.

\* cited by examiner

MEASUREMENT OF A COMPRESSION PARAMETER FOR CPR ON A SURFACE

CROSS REFERENCE TO RELATED PATENT APPLICATIONS

This patent application is a continuation of U.S. patent application Ser. No. 14/501,354, filed on Sep. 30, 2014, which itself is a continuation of U.S. patent application Ser. No. 12/579,455, filed on Oct. 15, 2009 and issued as U.S. Pat. No. 8,876,742 on Nov. 4, 2014, which itself claims priority from U.S. Provisional Patent Application Ser. Nos. 61/235,584, filed on Aug. 20, 2009, and 61/158,002, filed on Mar. 6, 2009, the disclosures of which are hereby incorporated by reference for all purposes.

TECHNICAL FIELD

This disclosure is related to the administration of cardiopulmonary resuscitation (CPR). In particular, this disclosure is related to a CPR assist device for the administration of CPR on a surface, such as a non-rigid or deformable surface.

BACKGROUND

There are currently an estimated 40,000 incidences of cardiac arrest every year in Canada, most of which take place outside of hospital settings. The odds of an out-of-hospital cardiac arrest currently stand at approximately 5%. In the U.S., there are about 164,600 such instances each year, or about 0.55 per 1000 population. It may be desirable to decrease the number of deaths resulting from these out-of-hospital incidences of cardiac arrest. Certain places, such as sports arenas, and certain individuals, such as the elderly, are at particular risk and in these places and for these people, a convenient solution may be the difference between survival and death.

Cardiopulmonary resuscitation (CPR) is an effective technique that enables medical and non-medical professionals to increase the chance of survival for patients experiencing cardiac failure. CPR forces blood through the circulatory system until professional medical help arrives, thereby maintaining oxygen distribution throughout the patient's body. However, the quality of CPR is often poor. Retention of proper CPR technique and protocol may be inadequate in most individuals and the anxiety of an emergency situation may confuse and hinder an individual in delivering proper treatment.

Therefore, a device to facilitate the proper delivery of CPR in an emergency may be useful. A number of devices exist to deliver objective feedback to a CPR administrator while delivering CPR, but these devices all possess a similar inadequacy. A recent study (Resuscitation. 2009 January; S0(1):79-82. Epub 2008 Oct. 25: 'Compression feedback devices overestimate chest compression depth when performed on a bed') unearthed a flaw affecting current CPR assist devices. The study indicates that CPR assist devices tend to overestimate chest compression depth when the patient receiving the CPR is on a non-rigid or deformable (e.g., compressible) surface, such as a mattress. The feedback device may erroneously register the movement of the mattress as part of the chest compression. A non-rigid or deformable surface below a patient during CPR may absorb a portion of the force applied by the CPR administrator to the chest of the patient. As a result, the surface beneath the patient may be compressed downward along with the patient's chest during the compression. Any compression measuring device placed on the chest of the patient will measure both the displacement of the chest as well as the displacement of the soft surface beneath the patient. Consequently, the device may underestimate chest compression depth ultimately resulting in shallow compressions during CPR. The calculation of other compression parameters, such as chest recoil or compression force, may also be negatively affected when CPR is performed on a non-rigid or deformable surface. For example, a deformation of about 0.5 cm or larger in the surface supporting the patient may result in unacceptably erroneous sensor measurements, in some situations.

One factor contributing to this problem is the choice of sensor used to measure the chest compression depth. For example, an accelerometer is typically unable to compensate for the movement of a deformable surface, such as a mattress, because its measurements are relative to the Earth rather than the surface beneath the patient. Any motion relative to the Earth will be recorded by the accelerometer. Furthermore, the sensor typically is not able to distinguish between various sources of movement.

Other CPR assist tools use mechanical force measurements as an indicator of chest compression depth. These devices are also prone to errors when the CPR is performed on a patient supported on a non-rigid surface. The force required to compress the patient's chest a certain distance is larger on a non-rigid surface due to that surface absorbing much of the applied force. However, the device is usually unable to differentiate between the force absorbed by the mattress and that absorbed by the victim's chest.

Presently, backboards and cardioboards are used to improve the transfer of force to the chest of a patient during CPR. A cardioboard is a relatively rigid or non-deformable support platform that may be slid or placed behind the back of the patient providing a solid, flat foundation between the mattress and the patient. The cardioboard may distribute the force over a larger surface area resulting in a smaller movement of the underlying mattress. A backboard operates in a similar way.

CPR on a non-rigid or deformable surface is a common situation in the clinical setting where CPR is often performed on a padded gurney or hospital bed. In other situations, potential non-rigid or deformable surfaces include outdoor soft turf, wet ground, or carpeted floor. It may be desirable to provide a device to take into account the motion and/or displacement of the surface when determining CPR parameters such as compression depth and rate when CPR is performed on a non-rigid or deformable surface. It may also be desirable to provide a device that may be used with currently available tools such as the cardioboard and the backboard.

SUMMARY

The present disclosure describes a device and method for the determination of at least one compression parameter during the administration of CPR on a patient that takes into account the motion and/or displacement of the surface supporting the patient, for example where the patient is supported by a non-rigid or deformable surface.

In some example embodiments, there is provided a device for the determination of at least one compression parameter during the administration of cardiopulmonary resuscitation (CPR) on a patient, the device comprising: a compression unit adapted to move in accordance with the chest of the patient, the compression unit having one of a signal component and a reference component; a surface unit adapted to move in accordance with a surface supporting the patient, the surface unit having the other of the signal component and the reference component; and a processor configured to determine a relative measurement between the compression unit and the surface unit using data derived from the signal component and the reference component, the processor being further configured to determine the at least one compression parameter based on the relative measurement; wherein the determined at least one compression parameter takes into account at least one of any motion of the surface and any displacement of the surface.

In the device described above, the signal and reference components may be motion sensors, position sensors, force sensors, pressure sensors, a field generator/field detector pair, or a signal transmitter/receiver pair. The device may also include a feedback component for providing feedback to a CPR administrator. The device may also include a base unit adapted to be stationary relative to a reference point.

The present disclosure also includes methods of determining CPR-related parameters, including compression parameters. For example, the device may be used to determine chest compression rate for CPR performed on a patient supported by a non-rigid surface. Some example embodiments may also be capable of determining patient size and determining the appropriate chest compression depth accord to the patient's body size. The device may also be capable of detecting the occurrence of ventilations to the patient and may be able to estimate ventilation volume.

BRIEF DESCRIPTION OF THE DRAWINGS

Aspects of the present disclosure will be discussed in detail below, with reference to the drawings in which.

DETAILED DESCRIPTION

In some example embodiments, the device includes a surface unit, a compression unit and a processor. The surface unit may be placed under the back, shoulder or neck of the patient and on the surface beneath the patient. Thus, the surface unit may be adapted to move in accordance with the surface supporting the patient, including compression, bounce, deformation or any other such motion and/or displacement of the surface. In some example embodiments, the compression unit may be positioned on the chest of the patient and under the hands of the CPR administrator. Thus, the compression unit may be adapted to move in accordance with the chest of the patient. The compression unit may include a signal component and the surface unit may include a reference component, or vice versa, for directly or indirectly sensing data for determining a compression parameter, such as compression depth.

The signal component and the reference component may be, for example, motion sensors (e.g., accelerometers or velocity sensors), pressure sensors, force sensors, position sensors such as a field generator/field detector pair, or a signal transmitter/receiver pair.

Combinations of different sensor types are also possible, for example wherein the reference component is a different type of sensor than the signal component. For example, the signal component may be an accelerometer, while the reference component may be a force sensor. It is also possible that one or both of the compression unit and surface unit may contain multiple signal or reference components, respectively. For example, the compression unit may contain two signal components, such as an accelerometer and a force sensor. Some examples are described in further detail below.

Figure 1:
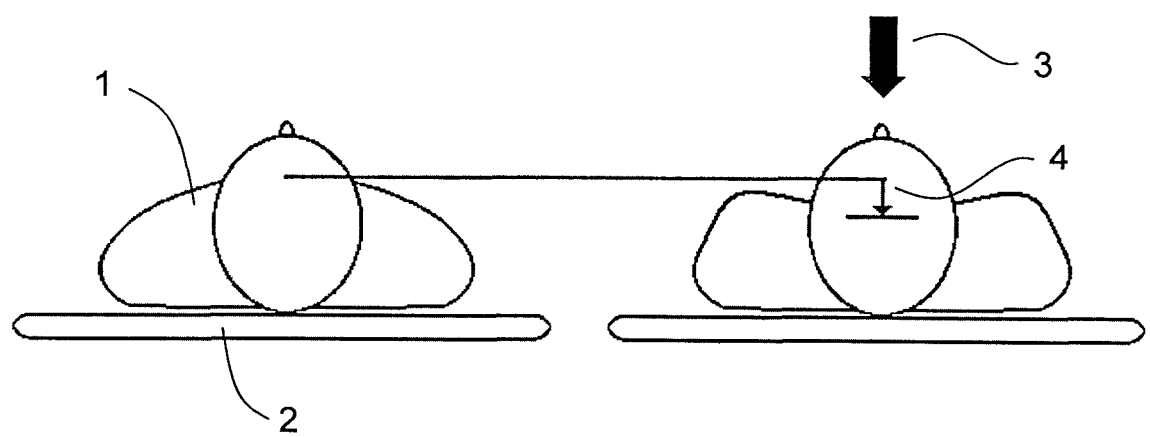
FIG. 1 is an illustration showing the displacement of a patient's chest during a compression when the patient is on a relatively rigid surface.
Figure 2:
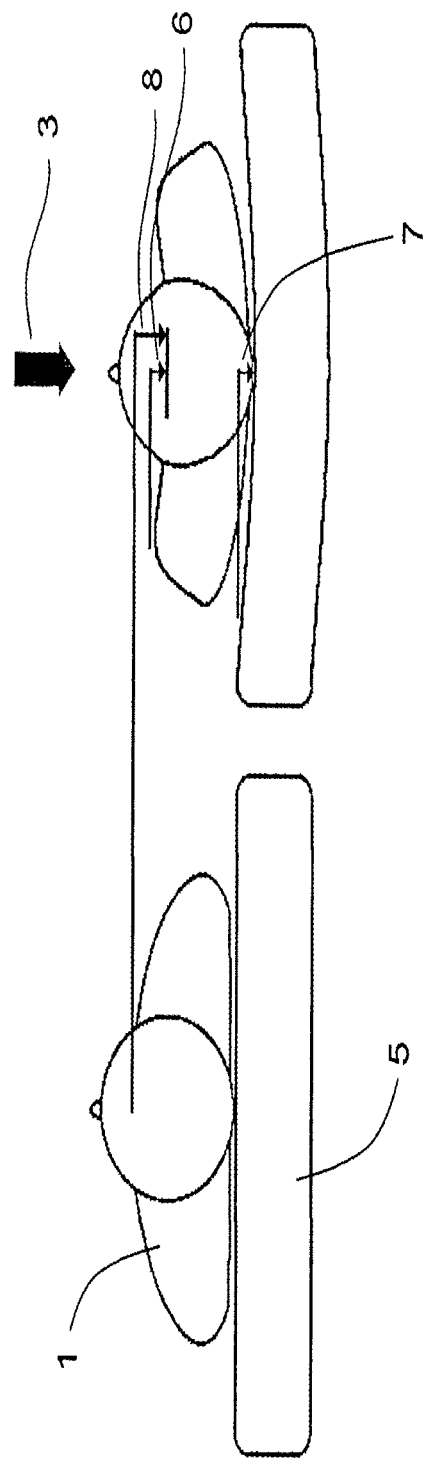
FIG. 2 is an illustration showing the displacement of a patient's chest and the displacement of the surface beneath the patient during a compression when the patient is on a non-rigid surface.

Reference is now made to FIGS. 1 and 2. FIG. 1 illustrates a patient 1 supported on a relatively firm non-deformable surface 2. When on a relatively firm non-deformable surface 2, the force 3 applied to a patient's chest is fully converted into downward displacement 4 of the chest. However, as shown in FIG. 2, when the patient 1 is supported on a non-rigid, flexible, pliant or otherwise deformable surface 5 during the administration of CPR, the surface 5 may absorb a portion of the force 3 applied by the CPR administrator to the chest of the patient. As a result, the surface 5 beneath the patient 1 may be compressed downward along with the patient's chest during the compression. A conventional chest compression measuring device placed on the chest of the patient 1 will measure both the displacement 6 of the chest as well as the displacement 7 of the surface 5 beneath the patient 1 resulting in a measured displacement 8 that is erroneously larger than the true depth 6 of the chest compression. Conventional devices using accelerometers and force sensors may be vulnerable to this problem as their measurements are not referenced to and do not take into account motion and/or displacement of the surface 5 under the patient 1. In general, motion and/or displacement of the surface 5 may refer to surface motion or displacement including compression, bounce, deformation, or bulk shifting of the surface 5. Consequently, a conventional CPR device containing such a sensor may underestimate chest compression depth ultimately resulting incorrect feedback being provided to the CPR administrator, which may lead to chest compressions that are unsuitably shallow.

Figure 3:
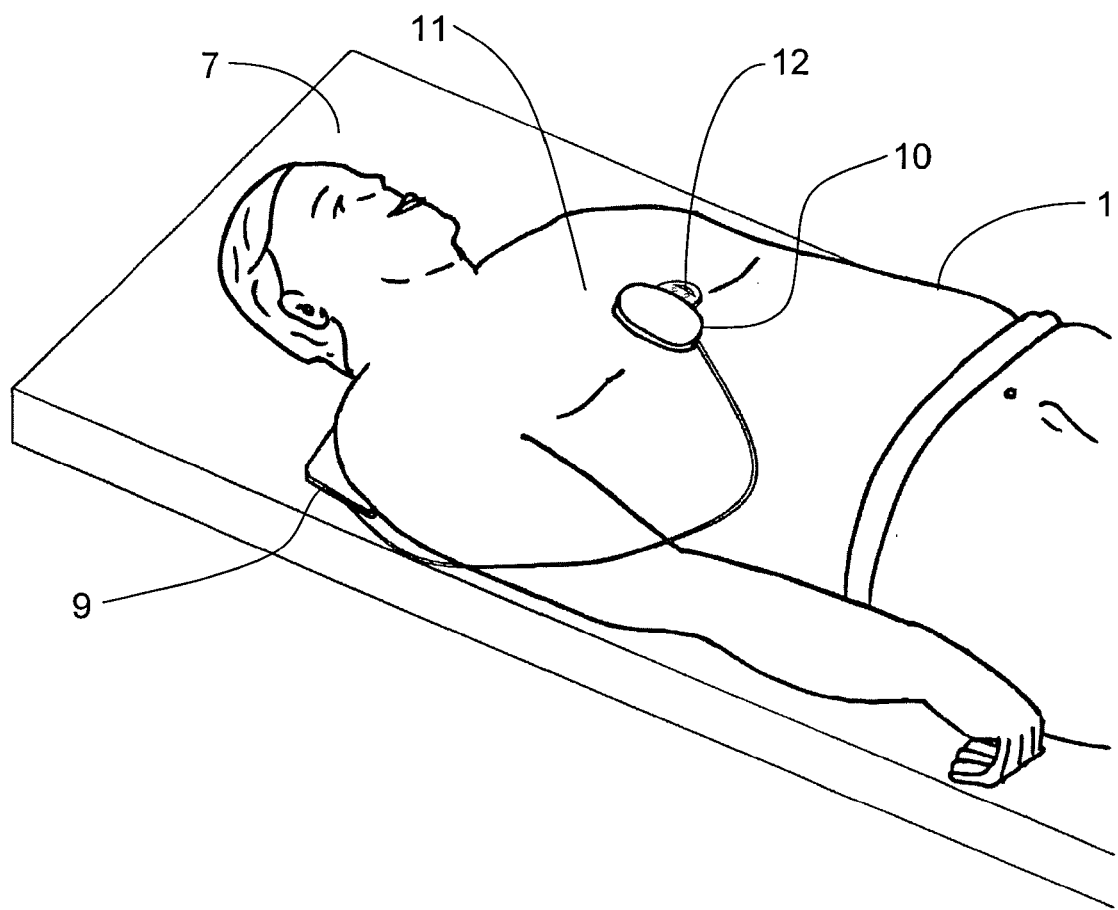
FIG. 3 is an illustration of an example embodiment of a CPR assist device in which a surface unit and compression unit are used to measure compression depth with feedback being provided by the compression unit.

Reference is now made to FIG. 3. The CPR assist device includes two units: a surface unit 9 and a compression unit 10. The surface unit may be placed under the patient 1, for example behind the back, shoulder or neck of the patient, on the surface 7 beneath the patient 1. The compression unit 10 may be positioned on the chest 11 of the patient 1 and under the hands of the CPR administrator (not shown). The compression unit 10 is adapted to move in accordance with the chest 11 of the patient 1, and the surface unit 9 is adapted to move in accordance with the surface 7. Each of the surface unit 9 and the compression unit 10 may be one of the reference component and signal component pair (not shown). The processor determines a relative measurement between the signal and reference components using data derived from the signal component and the reference component, and further determines a compression parameter (e.g., depth of chest compression, rate of chest compression) based on the relative measurement, taking into account motion and/or displacement of the surface 7. Since the surface unit 9 moves in accordance with the surface 7, calculations may be performed using the surface unit 9 as a reference point, thus taking into account motion and/or displacement of the surface 7 when determining the compression parameter.

Motion Sensors

Referring FIG. 3, in some examples, the signal component and the reference component may each be a motion sensor, such as an accelerometer or a velocity sensor. The reference component (e.g., an accelerometer) in the surface unit 9 under the patient 1 may be configured to sense the motion of the surface 7 (e.g., a mattress) as it is compressed during administration of CPR. The signal component (e.g., an accelerometer) may sense the motion of both the patient's chest 11 and the motion of the surface 7 beneath the patient 1. At the processor, the motion data (e.g., acceleration, velocity or displacement data) obtained from the reference component may be subtracted from the data obtained by the signal component, obtaining a relative measurement to account for any motion of the surface 7. For example, the affect of the motion of the surface 7 may be eliminated from the sensed motion of the chest 11.

In some examples, the signal component and the reference component are each accelerometers, each sensing signal and reference acceleration measurements, respectively. The processor may integrate the acceleration measurements, obtaining signal and reference velocity measurements, respectively. The processor may integrate the velocity measurements to obtain signal and reference displacement measurements, respectively. The signal displacement measurement may be indicative of the displacement of the signal component and the reference displacement measurement may be indicative of the displacement of the reference component. For example, where the signal component is in the compression unit and the reference component is in the surface unit, the signal and reference displacement measurements may be indicative of the displacement of the compression unit and the surface unit, respectively. The processor may subtract the reference displacement measurement from the signal displacement measurement to obtain the relative displacement measurement between the signal component and the reference component. In this manner, the affect of the motion of the surface 7 (as indicated by the displacement of the surface unit) may be taken into account.

Sensors other than accelerometers or velocity sensors may be used for motion sensing. For example, the signal component and/or the reference component may be force or pressure sensors. Where force sensors are used, the force data measured by the signal component may be subtracted from the data obtained by the reference component to account for the motion of the surface 7.

In some examples, a force sensor may be used as an indirect method of measuring motion. For example, the force absorbed by the surface may be measured by the force sensor and the corresponding deformation of the surface may be calculated based on this force measurement. Similarly, the displacement of the chest may be calculated by knowing the force required to compress the chest. The two displacements may be subtracted to remove the surface movement (i.e., the force required to further compress the surface).

In some examples, combinations of sensors are also possible wherein the reference component may be a different type of sensor than the signal component. For example, the compression unit may contain an accelerometer to measure chest and surface displacement and the surface unit may contain a pressure sensor to determine the amount of force transferred to the surface. The force data may be used to calculate an approximate deformation of the surface and the calculated displacement of the surface may be subtracted from the calculated displacement of the compression unit.

Field Generator and Field Detector

In some examples, the signal component may be a field detector for detecting a field (e.g., an electromagnetic field) and the reference component may be a field generator for generating a field (e.g., an electromagnetic field). The field generator and field detector may be an example of position sensors suitable for the disclosed device. Conversely, the signal component may be the field generator and the reference component may be the field detector. The field generator may include a coil assembly configured to generate a field, such as a varying electromagnetic field, and the field detector may include a coil assembly configured to detect the generated field. The coils of the field generator and field detector may include multiple wire windings on multiple axes so as to produce multiple fields in multiple directions. Multiple windings, which in some examples are orthogonal to each other, may enable the determination of a three-dimensional position coordinate. The data derived from the signal component and the reference component, in this example, is a response signal from the field detector that is responsive to the field generated by the field generator. In some examples, the response signal is indicative of the field strength sensed by the field detector. The processor may use data from the signal and reference components, such as a signal indicating the strength of the electromagnetic field, to calculate the relative measurement, in this example being the position of the field detector relative to the field generator. From the relative position information, the compression parameter, such as chest compression depth, may be calculated. For example, the reference component may be the field generator, and may be placed behind the patient's back; the signal component may be the field detector, and may be positioned on the patient's chest. Since the position of the field detector is determined relative to the position of the field generator and the field generator is in the surface unit that moves in accordance with the surface, displacement of the chest can be determined separate from the displacement of the surface.

Figure 5:
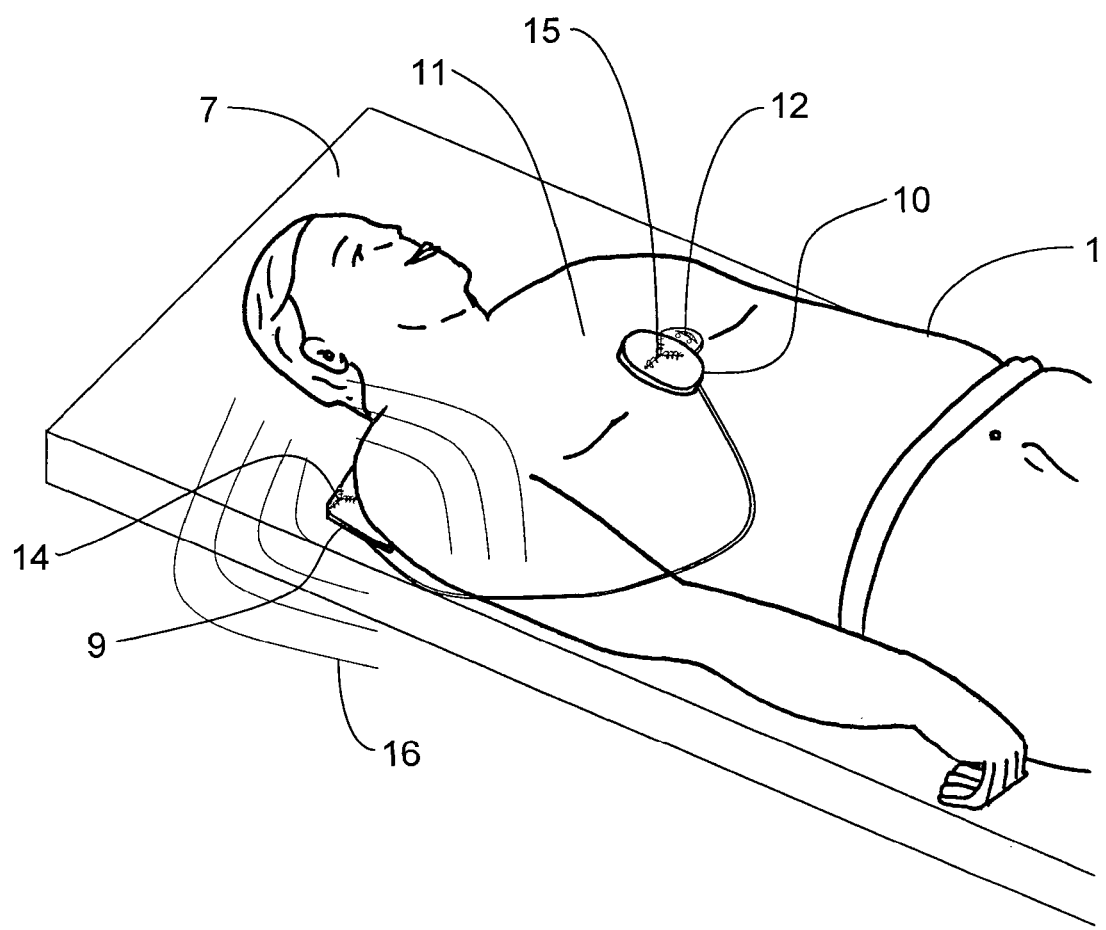
FIG. 5 is an illustration of an example embodiment in which the surface unit contains a field generator and the compression unit contains a field detector.
Figure 6:
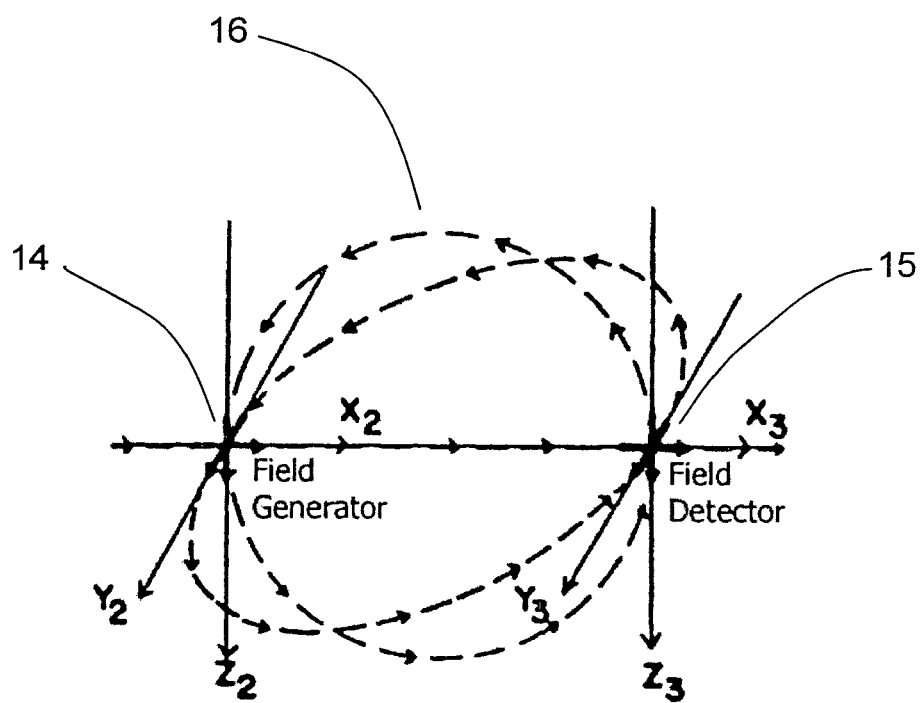
FIG. 6 is a diagram showing the generation and detection of electromagnetic fields, in an example.

Reference is now made to FIG. 5. In the example shown, the signal component and the reference component are a pair of field generator 14 and field detector 15. For example, the field generator 14 may be an electromagnetic field generator and the field detector 15 may be an electromagnetic field detector. In the example shown, the reference component in the surface unit 9 is the field generator 14 and the signal component in the compression unit 10 is the field detector 15, however in other examples, the reference component may instead be the field detector 15 and the signal component may instead be the field generator 14. The field generator 14 may be configured to generate an electromagnetic field 16 and the field detector 15 may be configured to detect the electromagnetic field 16. For example, the field generator 14 and the field detector 15 may each include coil assemblies for generating and detecting the electromagnetic field 16, respectively. FIG. 6 illustrates an example of electromagnetic fields 16 that may be generated and detected by the field generator 14 and field detector 15, respectively.

Figure 7:
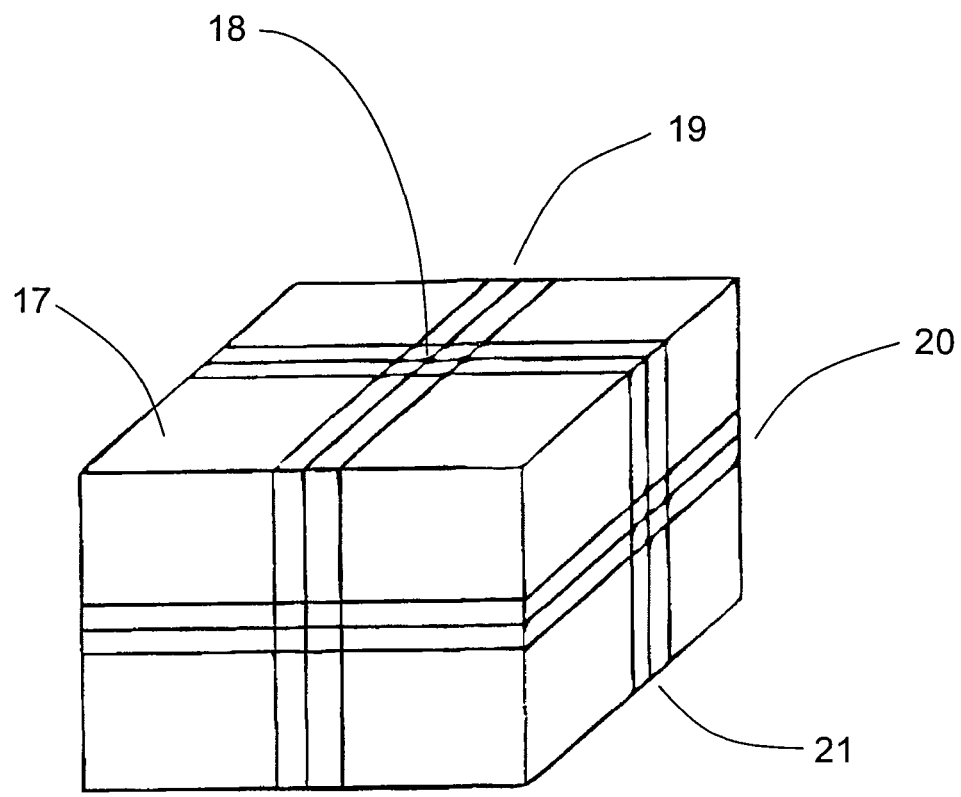
FIG. 7 is an illustration showing an example coil assembly for the field generator or field detector.

Reference is now made to FIG. 7, illustrating an example coil assembly 17 suitable for use in the field generator 14 and the field detector 15. The coil assembly 17 may be configured to have multiple windings 18 on multiple axes so as to generate or detect multiple fields in multiple directions. In some examples, the coil assembly 17 may contain three distinct coils wound on each of the x 19, y 20 and z 21 axes so as to produce three perpendicular electromagnetic fields. Examples of suitable field generators and detectors are described in U.S. patent application Ser. No. 12/354,913, the entirety of which is hereby incorporated by reference. Detection of the generated field by the field detector 15 produces a response signal that is transmitted or otherwise provided to the processor of the CPR assist device. The response signal may, in some examples, be indicative of the field strength detected by the field detector 15. Using the response signal (e.g., being indicative of the field strength detected), the processor determines the position of the field detector 15 relative to the field generator 14. From the determined position information, the compression parameter, such as chest compression depth, may be determined, for example as described in U.S. patent application Ser. No. 12/354,913.

In some examples, a wireless synchronization signal may be transmitted between the surface unit 9 and the compression unit 10 to ensure that the field detector 15 is synchronized to the field generator 14. In examples where the generator coil assembly 17 contains multiple coils (e.g., three coils), the fields generated by each coil may be time-multiplexed and sequenced on each of the three coils. A synchronization signal may indicate to the field detector 15 which coil is generating the field being detected. In some examples, generated fields are frequency multiplexed across all the coils. In this case, a synchronization signal may not be necessary as all the generated fields may be generated simultaneously, but at different frequencies. The field detector 15 may detect each field separately, for example through the use of bandpass filtering for each distinct frequency or frequency band, and measuring the field strength at that frequency or frequency band. Examples of suitable methods are described in U.S. application Ser. No. 12/354,913.

Because the reference component is adapted to move in accordance with the surface 7 supporting the patient 1, the effect of the surface's displacement can be taken into account, for example by eliminating any surface displacement from determination of the compression parameter. For example, where the reference component is the field generator 14, the processor determines the position of the field detector 15 (in this example, the signal component) relative to the position of the field generator 14 (in this example, the reference component). Because the field generator 14 is moving with the surface 7, the displacement of the chest is determined relative to displacement of the surface 7.

Figure 9:
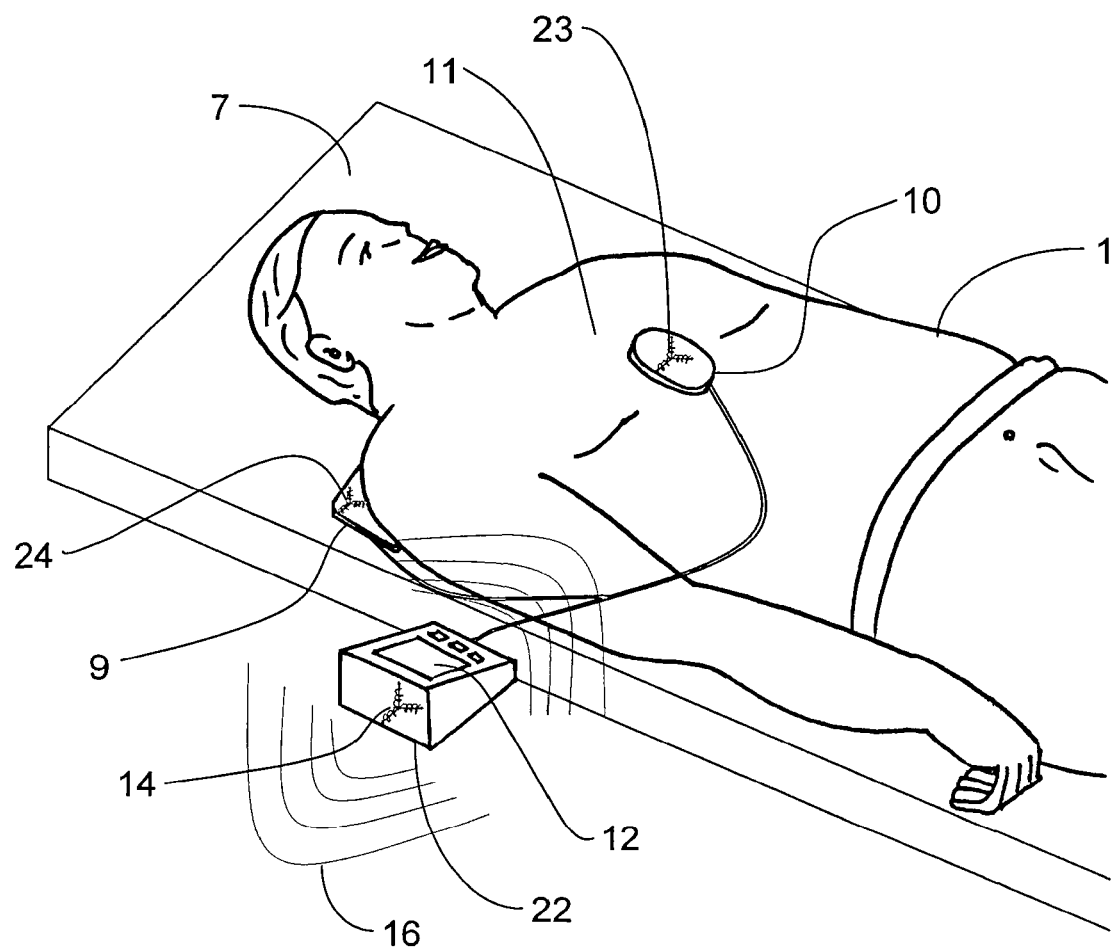
FIG. 9 is an illustration of an example embodiment in which the surface unit and compression unit each contain a field detector while a separate base unit contains a field generator.

In some examples, the CPR device may include a separate base unit 22 as shown in FIG. 9. In this example, the signal component and the reference component are first and second field detectors 23, 24, and the field generator 14 is provided in the base unit 22. Each of the field detectors 23, 24 detects the field generated by the field generator 14 and provides respective first and second response signals to the processor. The processor uses the respective response signals to determine the position of each of the field detectors 23, 24 (and by extension each of the compression unit 10 and the surface unit 9) relative to the base unit 22. The base unit 22 may be positioned stationary relative to a reference point (e.g., a stationary flood), for example on a relatively rigid surface adjacent to the patient 1. Thus, the processor may determine position of the surface unit 9 relative to the base unit 22, and this position is indicative of the position (including any displacement) of the surface 7 supporting the patient 1. Similarly, the processor may determine position of the compression unit 10 relative to the base unit 22. The processor may then determine position of the compression unit 10 relative to the reference unit 9 and thus take into account any displacement of the surface 7. For example, the position of the field detector 24 in the surface unit 9 may be subtracted from the position of the field detector 23 in the compression unit to eliminate any error in the determination of a compression parameter, such as chest compression depth, resulting from displacement of the surface 7.

Transmitter and Receiver

In some examples, the reference component may be a signal transmitter and the signal component may be signal receiver. In this example, the data derived from the signal and reference components is a sensed time-of-flight of the signal from the transmitter to the receiver. The time-of-flight of the transmitted signal may be measured by the receiver as it is intercepted. The time-of-flight calculation (i.e., elapsed time from signal emission by the transmitter to signal reception by the receiver) may be used by the processor to determine the relative measurement between the signal and reference components, in this example being the distance between the surface unit and compression unit. For example, the transmitter and receiver may be designed to transmit and receive signals such as ultrasound signals, radio frequency signals, optical signals and others.

Figure 10:
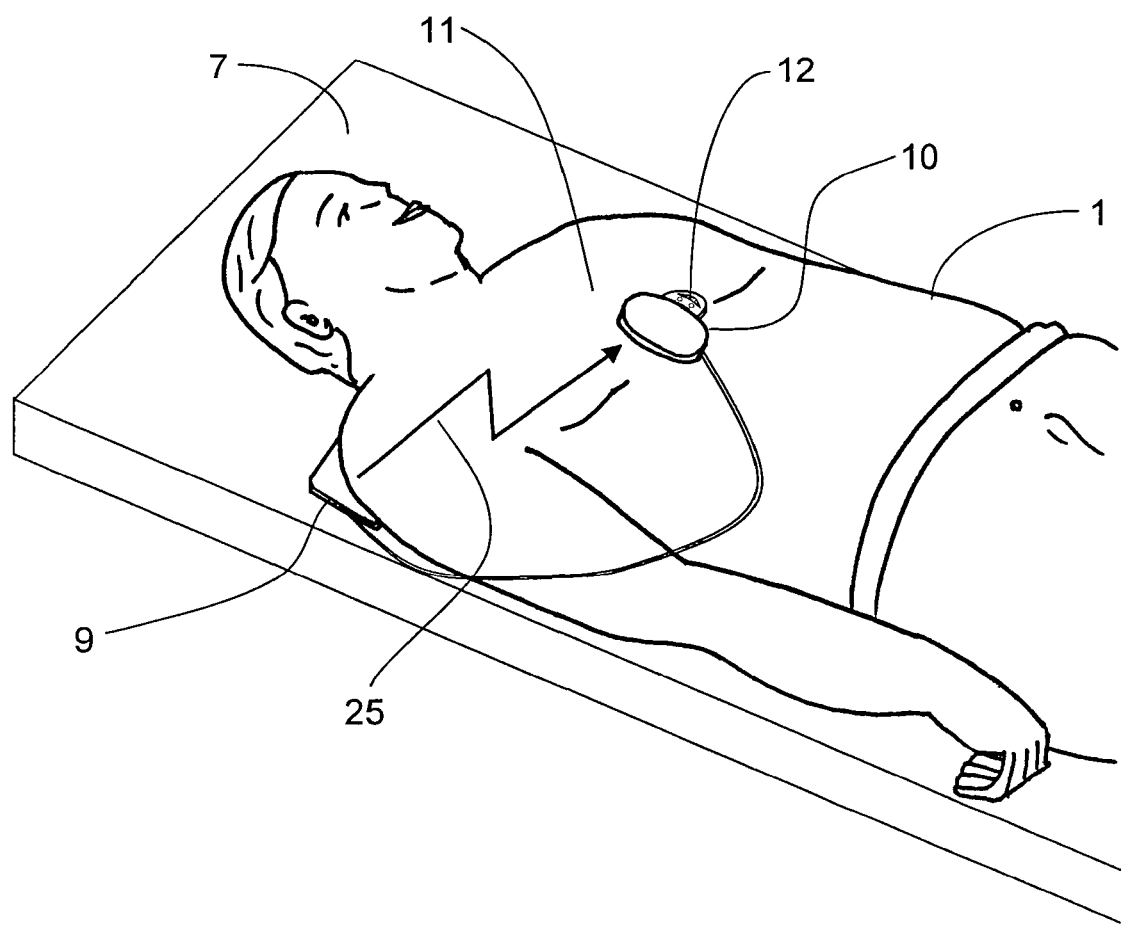
FIG. 10 is an illustration of an example embodiment in which the surface unit contains a signal transmitter and the compression unit contains a signal receiver.

Reference is now made to FIG. 10. In the example shown, the reference component is in the surface unit 9 and is a signal transmitter, and the signal component is in the compression unit 10 and is a signal receiver. In other examples, the reference component may be the signal receiver and the signal component may be the signal transmitter. The transmitter transmits a signal 25 to the receiver. The distance between the receiver (and by extension the compression unit 10) and the transmitter (and by extension the surface unit 9) may be determined by the processor based on the strength of the received signal (e.g., as sensed by the receiver) or the time-of-flight of the received signal at the receiver. For example, if the transmitter sends an ultrasound signal, the receiver may measure the time interval between signal emission and signal reception. A known relationship between this time interval and distance (e.g., based on a known speed of transmission of the ultrasound signal) may be used at the processor to determine the position of the compression unit 10 relative to the surface unit 9. As the position of the compression unit 10 is determined relative to the surface unit, and the surface unit 9 moves in accordance with the surface 7 supporting the patient 1, the motion and/or displacement of the surface 7 may be taken into account in determining the compression parameter, for example by reducing or eliminating the influence of any motion and/or displacement of the surface 7. The transmitter and receiver may be configured to transmit and receive, respectively, different types of signals, for example ultrasonic signals, optical signals, radio frequency signals, ultra wideband signals, acoustic signals, infrared signals, or any other suitable signals.

Force Sensors

In some examples, the reference component and signal components are force sensors. In examples where the signal and reference components are force sensors, the force measurement sensed by the reference component may be subtracted from the force measurement sensed by the signal component to account for surface movement. This may be similar to the calculations based on motion sensors, as described above.

The force sensor may be used in combination with other sensor modalities. Since chest and surface compliances typically vary from patient to patient and surface to surface, determination of compression parameters, such as chest compression depth, may be inaccurate based on simple force measurements. Force measurements may be useful to augment the use of other sensor types. For example, if the signal component and force sensors are accelerometers and the determined compression parameter is chest compression depth, one source of error may be surface bounce (e.g., where the surface is a flexible or elastic surface such as a mattress). At the top and bottom of a chest compression, the surface may vibrate or bounce resulting in inaccurate position and depth measurements. By incorporating a force sensor into the compression unit, the device is able to determine when actual force is being applied to the patient's chest.

Figure 11:
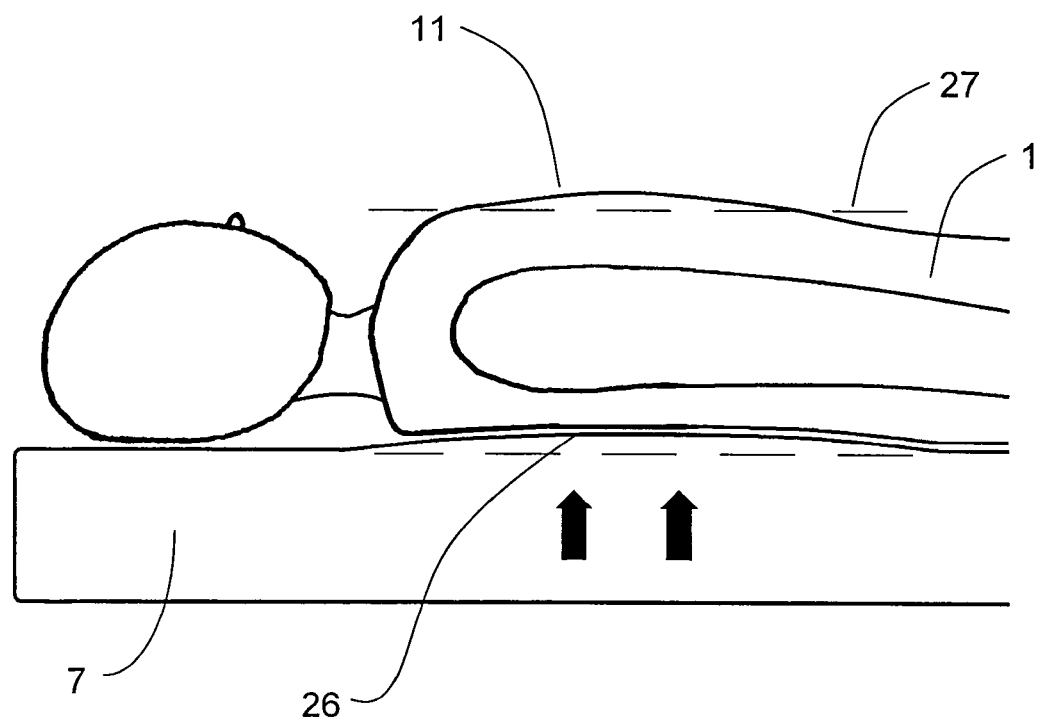
FIG. 11 is a side view of a patient on a non-rigid surface showing surface bounce at the top of a chest compression.

Reference is now made to FIG. 11. Surface bounce may be a significant source of error when determining chest recoil on a patient 1 supported on a non-rigid surface 7. Proper chest recoil requires the CPR administrator to fully release the chest 11 of the patient 1 at the top of a chest compression. This recoil allows the blood to refill the chambers of the heart, so as to be re-circulated at the next compression. During recoil, there should be little or no force applied by the CPR administrator to the chest 11 of the patient 1. However, due to there being no external force applied by the CPR administrator during this phase, the surface 7 below the patient 1 may rebound 26, causing the chest 11 to move slightly beyond the starting point 27 of the chest compression. This bounce effect may reduce the accuracy of determination of compression parameters, such as chest compression depth, and may also prevent the proper determination that recoil has been fully achieved. The addition of a force or pressure sensor to the compression unit may help to reduce or eliminate erroneous data due to surface bounce since this motion occurs in the absence of applied force. Using the pressure and force data, this bounce motion may thus be taken into account in determining the compression parameter. For example, any motion determined in the absence of any sensed force may be ignored or discarded by the processor.

Feedback Component

The CPR assist device may include a feedback component for providing feedback to the CPR administrator based on the determined compression parameter. For example, the feedback component may be provided on one of the compression unit 10 and the surface unit 9, for example as shown in FIGS. 3, 5, 10, 12 and 13. Providing feedback on the compression unit 10 allows visual feedback to be presented to the CPR administrator while CPR is being administered. In such an example, the feedback component may be a screen or display. The feedback component may also be an audio or tactile component to provide audio or tactile feedback to help coach the CPR administrator during the administration of CPR. Suitable feedback components and their configuration may include those described in U.S. patent application Ser. Nos. 12/354,913 and 11/936,184, both of which are hereby incorporated by reference in their entirety.

Figure 4:
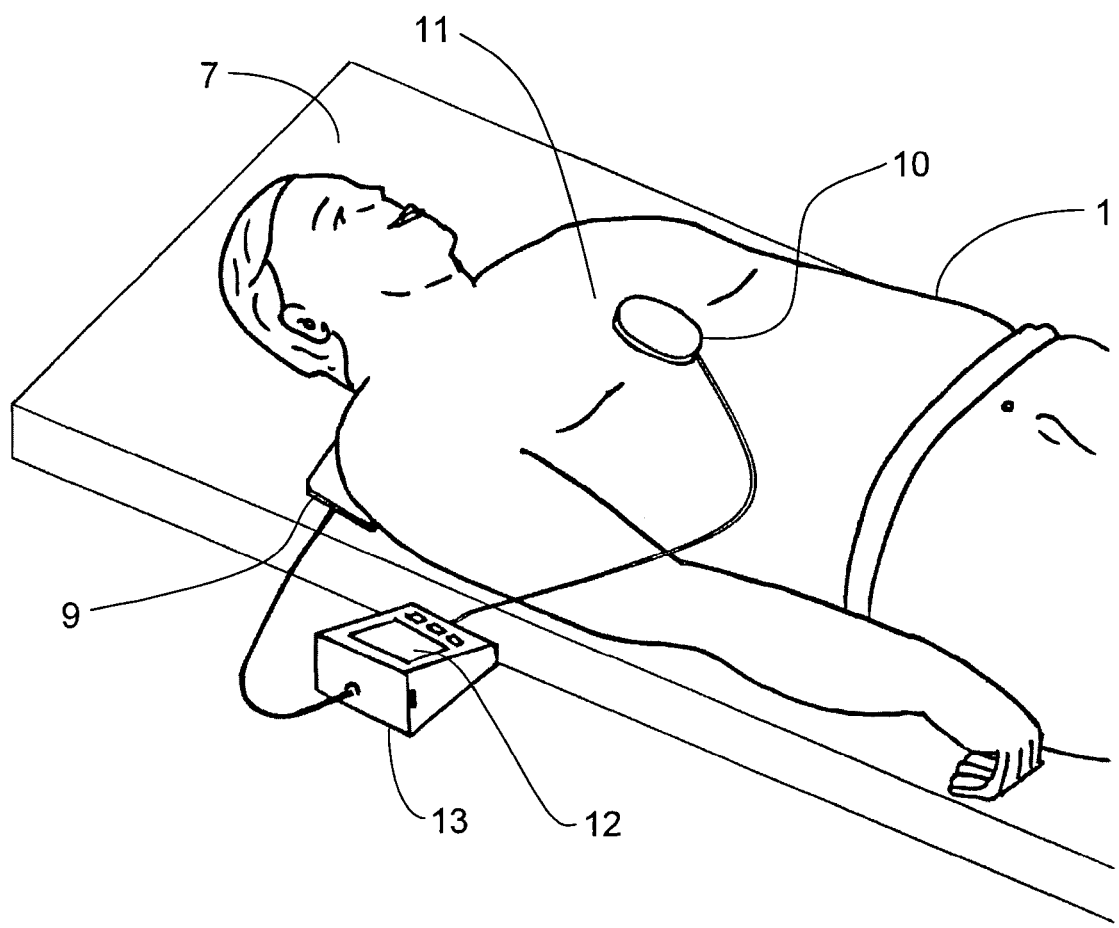
FIG. 4 is an illustration of an example embodiment in which a surface unit and compression unit are used to measure compression depth with feedback being provided by a separate base unit.

Reference is now made to FIG. 4. In some examples, the device includes a base unit 13, and the feedback component 12 is provided in the base unit 13. The base unit 13 may be positioned near the patient, for example on the floor beside the patient, so that feedback (e.g., visual and/or audio feedback) may be provided separate from the surface unit 9 and compression unit 10. In the example shown, the base unit 13 may accommodate a feedback component 12 that is more enhanced, such as a larger visual display or enhanced audio quality component, than when the feedback component is directly integrated into the compression unit 10 or the surface unit 9. The base unit 13 may also contain additional components, such as a memory for data storage and a processor interface (e.g., a program menu) allowing the CPR administrator flexibility in the amount and type of feedback provided.

Figure 8:
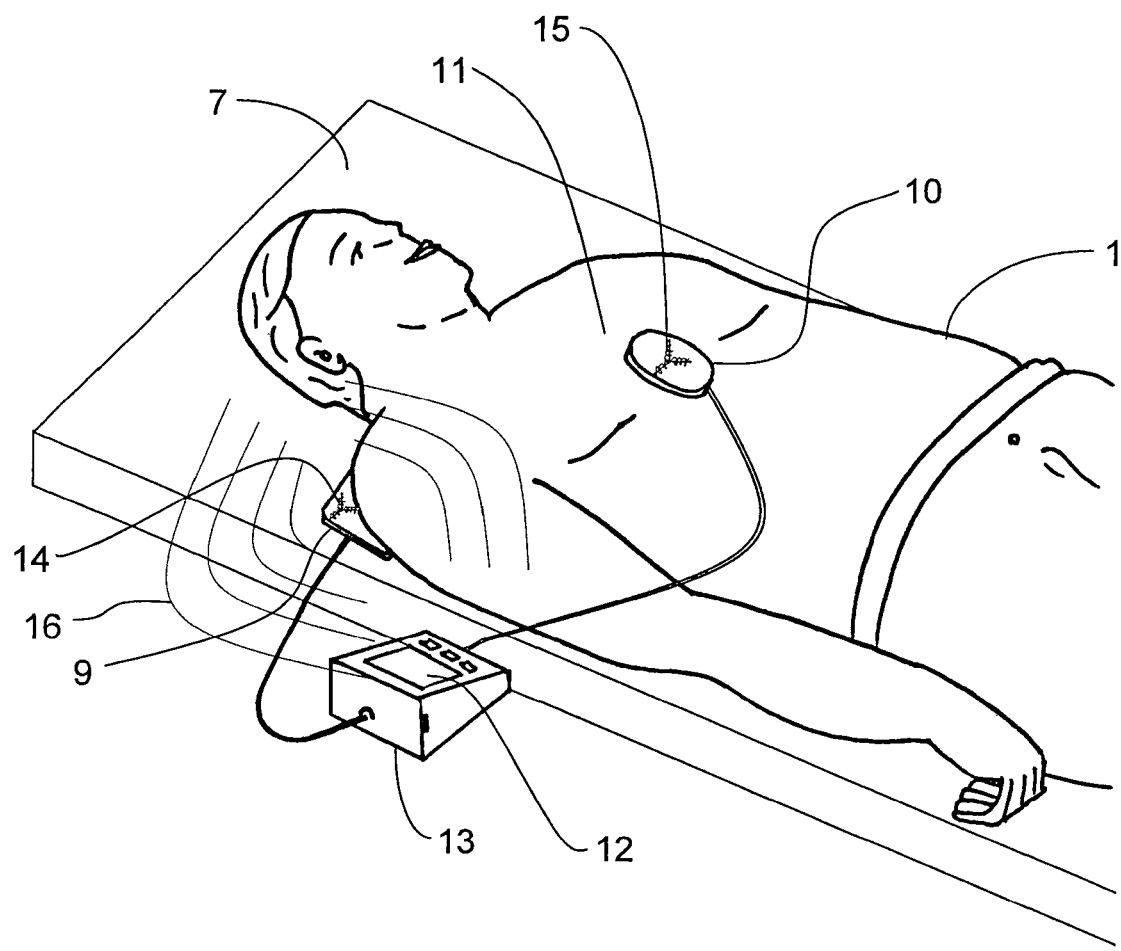
FIG. 8 is an illustration of an example embodiment in which the surface unit contains a field generator and the compression unit contains a field detector, and there is a separate base unit to provide feedback.

Reference is now made to FIG. 8. This figure illustrates another example in which a base unit 13 provides a feedback component 12, in this case where the signal component and reference component are a field detector 15 and field generator 14, respectively.

Physical Variations

Figure 12:
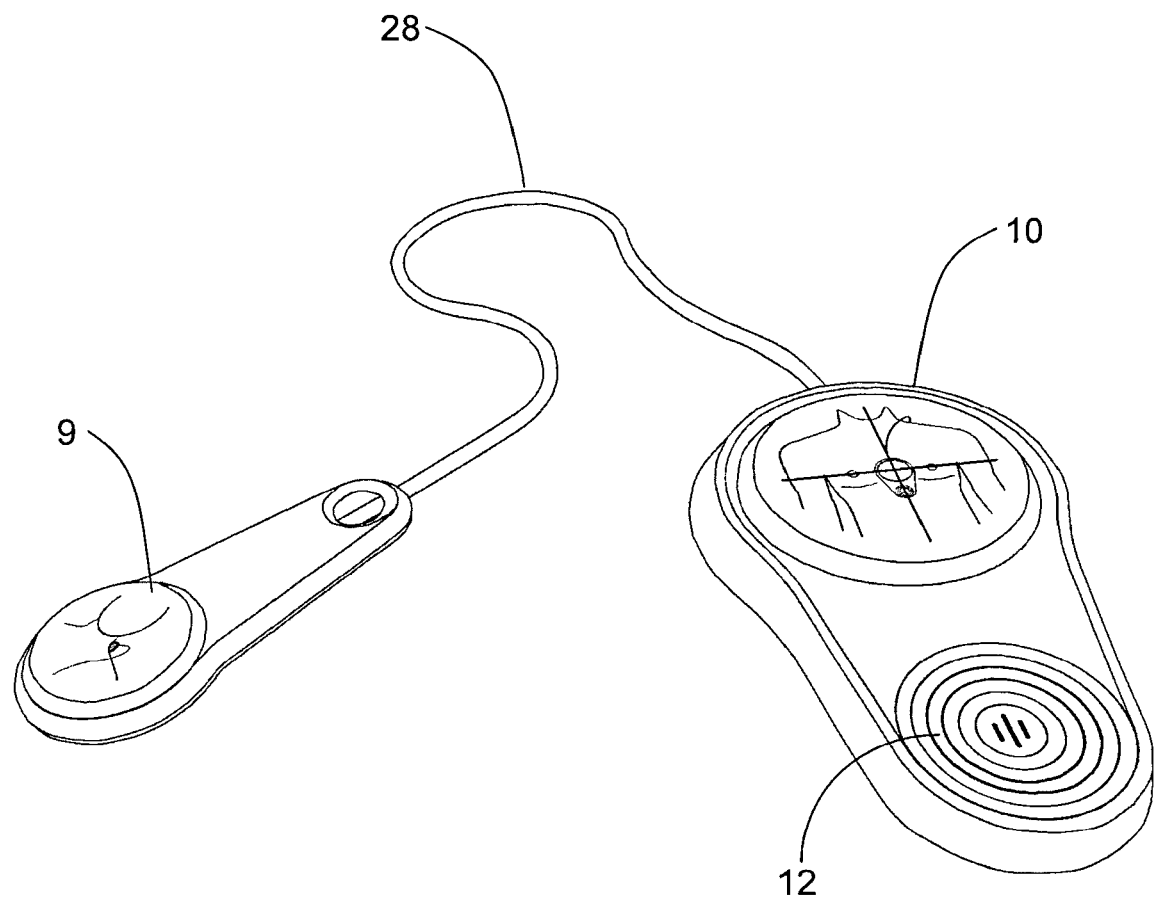
FIG. 12 is an illustration of an example embodiment in which a surface unit is tethered to a compression unit.
Figure 13:
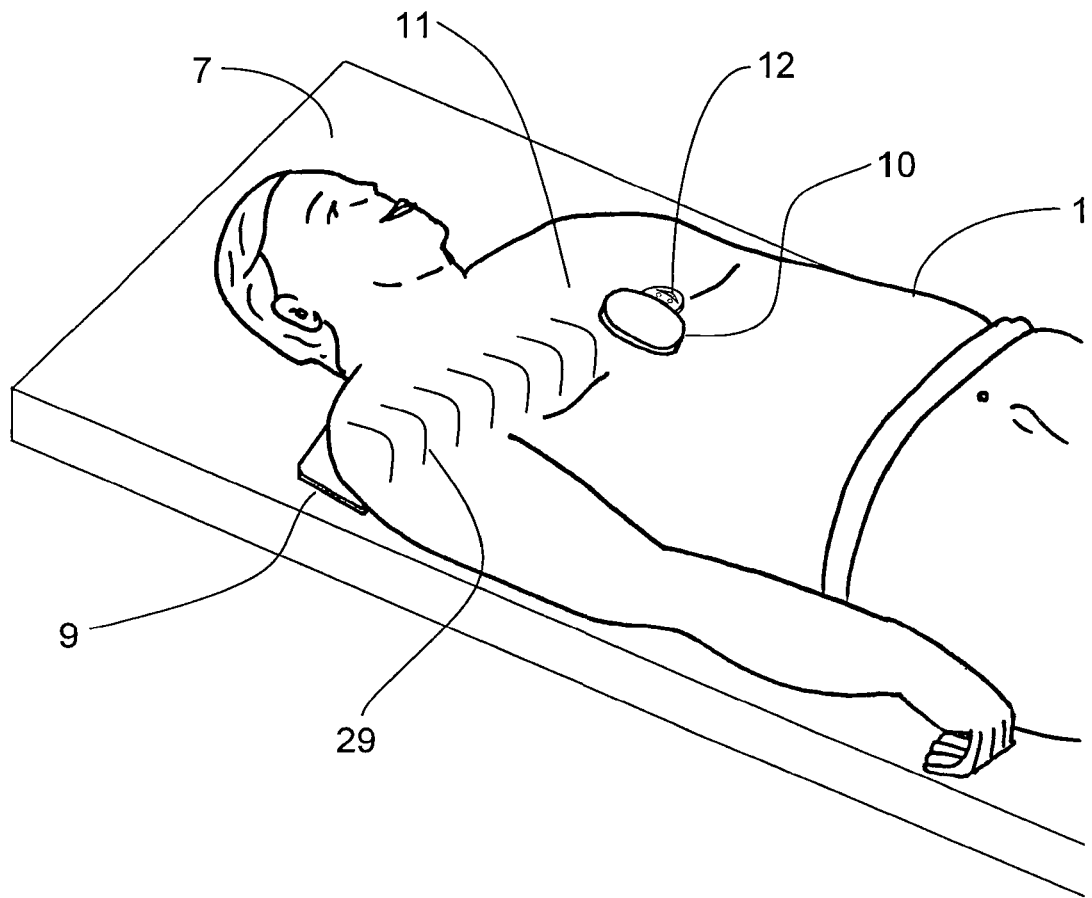
FIG. 13 is an illustration of an example embodiment in which the surface unit communicates with the compression unit wirelessly.

Reference is now made to FIG. 12. In some examples, the surface unit 9 and the compression unit 10 may be connected to each other, for example by a tether 28, a cable or a connector. In other examples, there may be no physical connection between the surface unit 9 and the compression unit 10. For example, where communication between the surface unit 9 and the compression unit 10 is useful (e.g., where the processor is contained in one of the surface unit 9 and the compression unit 10) a wireless data communication path 29 may be established as shown in FIG. 13. Data from either the compression unit 10 or the surface unit 9 may be sent to the unit containing the processor for processing. For example, if the surface unit 9 contains the processor, the compression unit 10 may have a wireless transmitter capable of sending data sensed by the signal component to the surface unit 9. The data may be sent by any wireless means, for example including radio frequency, Bluetooth, Wi-Fi, infrared and any other suitable methods.

In some examples, communication between the surface unit 9 and the compression unit 10 may be inherently wireless, without the need for a separate wireless transmitter for the purpose of data transmission. For example, where the reference component in the surface unit 9 is a field generator and the signal component in the compression unit 10 is a field detector, generation and detection of a field is inherently wireless. The data from the signal and reference components is based on the detection of the generated field and the field is perpetuated wirelessly through free space.

Figure 14:
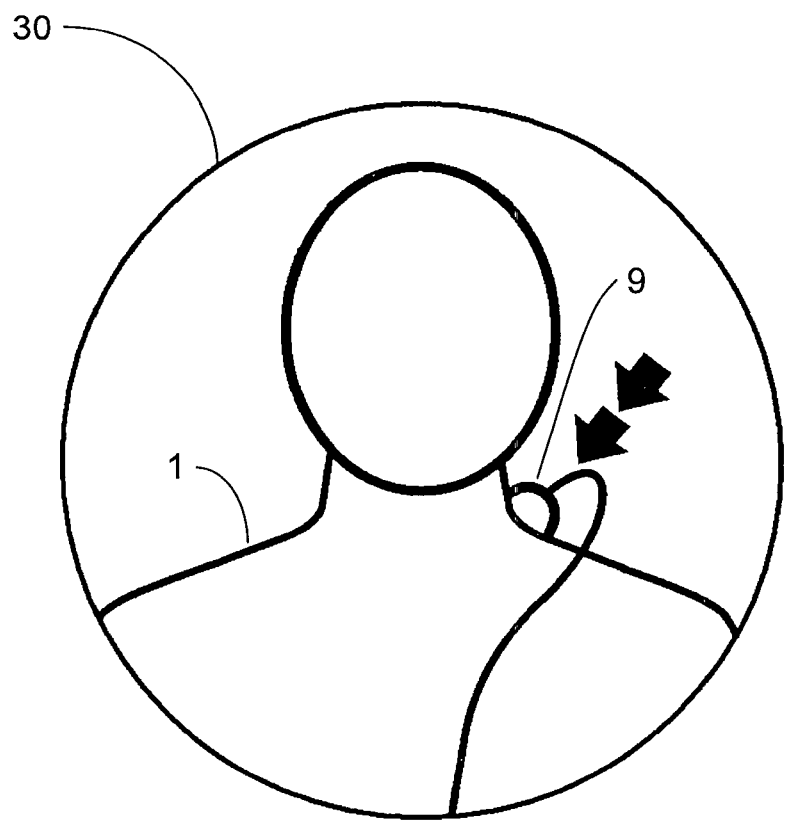
FIG. 14 is a diagram depicting an example label for the surface unit.

Although the presently disclosed device has been described in certain physical configurations, variations are possible. In some examples, such as that shown in FIG. 3, the surface unit 9 may be positioned so that it is behind the back of the patient 1 and on top of the surface 7. The compression unit 10 may be positioned so that it is on the chest 11 of the patient 1 and under the hands of the CPR administrator. The surface unit 9 should be positioned so that it moves in accordance with the surface 7 beneath the patient 1. The compression unit 10 should be positioned so that it moves in accordance with the chest 11 of the patient 1. When the compression unit 10 and the surface unit 9 are thus positioned, it is possible for the process to take into account motion and/or displacement of the surface 7, for example by eliminating the effect of the surface 7 by subtracting the displacement of the surface unit 9 from the displacement of the compression unit 10, resulting in a determination of the displacement of the patient's chest 11 without the influence of surface displacement. Suitable positioning of the surface unit 9 may be indicated to the CPR administration, for example through the use of a diagram 30 on the surface unit 9 depicting proper positioning as shown in FIG. 14.

When placing the surface unit 9, the exact position of deployment behind the patient's back may be important. For example, proper placement of the surface unit 9 may allow the surface unit 9 to move in accordance with the entire motion and/or displacement of the surface 7 (e.g., motion or displacement of the surface unit 9 is identical with respective motion or displacement of the surface 7) or with a portion of the motion and/or displacement of the surface 7 (e.g., motion or displacement of the surface unit 9 is a fraction of the respective motion or displacement of the surface 7). However, regardless of whether the surface unit 9 moves with the entire motion and/or displacement or with a portion of the motion and/or displacement of the surface 7, in both cases the surface unit 9 is considered to move in accordance with the surface 7.

Figure 15:
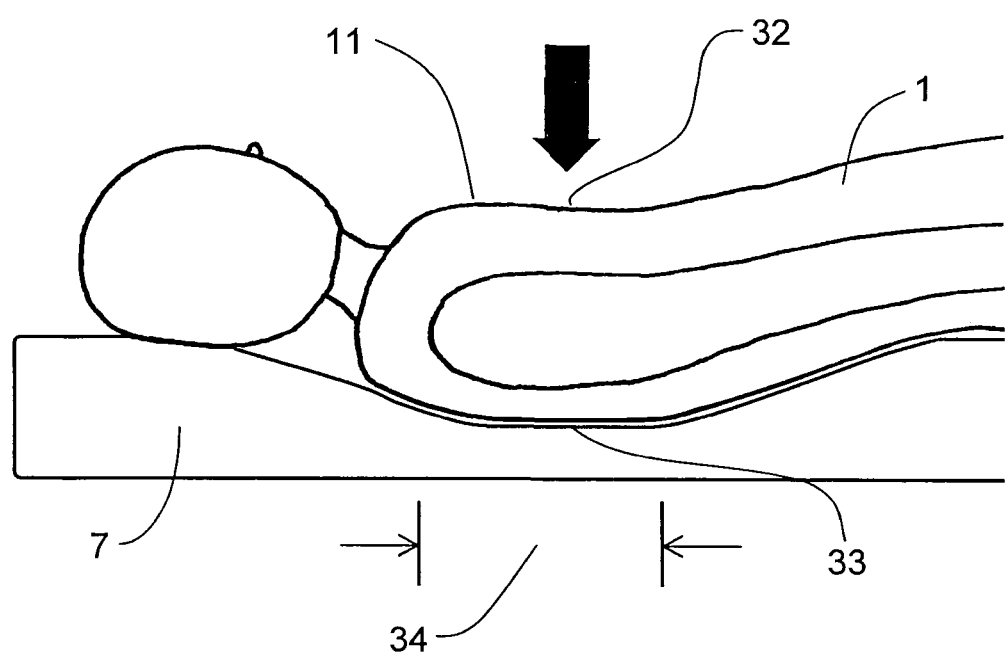
FIG. 15 is a side view of a patient on a non-rigid surface showing the deformation of the non-rigid surface at the deepest point of a chest compression.
Figure 16:
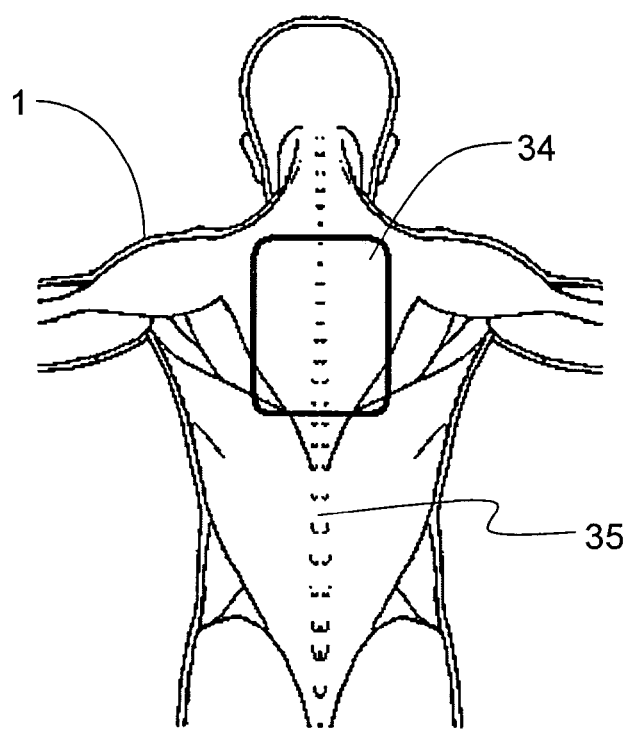
FIG. 16 is a an illustration showing the reduced-flex zone on the back of a human.
Figure 17:
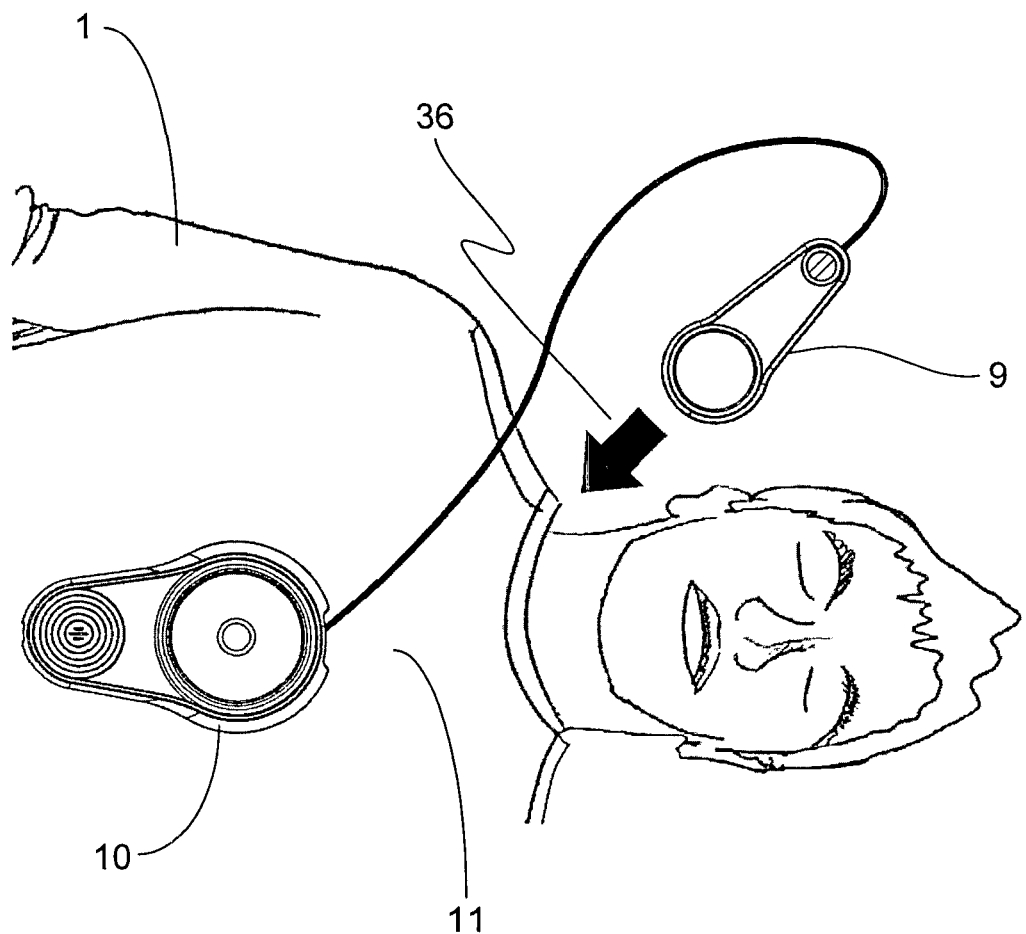
FIG. 17 is an illustration showing an example of the surface unit being slid under the shoulder and back of a patient.

As shown in FIG. 15, when a chest compression is delivered, the surface 7 behind the back of the may flex so that its deepest point is directly below the point of compression 32. The surface 7 below the point of compression 32 is concave and becomes less so further from the point of compression 32. Therefore, placement of the surface unit 9 close to the area 33 of the surface 7 directly below the point of compression 32 may more fully capture the motion and/or displacement of the surface 7. There is generally thought to be a reduced-flex zone 34 in the human back behind the point of compression 32 as depicted in FIG. 16. This reduced-flex zone 34 remains relatively flat during a chest compression due to the rigidity of the spine 35 in this area. Therefore, the surface 7 in the vicinity of the reduced-flex zone 34 will remain relatively level and flat during a compression, thus may represent the deepest point of concavity of the surface, and thus it may be useful to position the surface unit 9 in this area. While positioning the surface unit 9 within or near the reduced-flex zone 34 may be useful, placement anywhere behind the back, shoulder or neck of the patient 1 may still allow the surface unit 9 to move in accordance with the surface 7. In the example shown in FIG. 17, the compression unit 10 may be positioned on the chest 11 of the patient 1 and the surface unit 9 may be positioned (e.g., by a sliding motion 36) under the shoulder of the patient 1 and into the reduced-flex zone 34.

When the surface unit 9 is positioned outside the reduced-flex zone 34 or in a location where the surface unit 9 may follow only a portion of the motion and/or displacement of the surface 7 under the point of compression, certain techniques may be used to reduce error and help estimate the full motion and/or displacement of the surface 7. For example, each of the surface unit 9 and the compression unit 10 may include a force sensor as the reference component and the signal component, respectively, and additionally each include a motion or position sensor (e.g., an accelerometer or a field generator/field detector pair) for sensing translational data.

Figure 18:
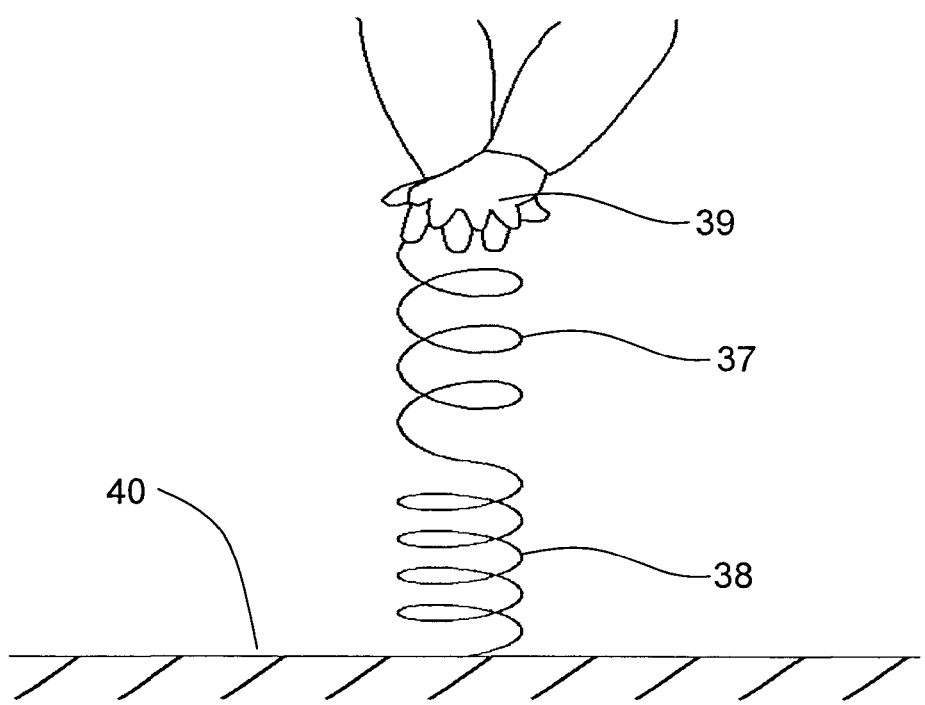
FIG. 18 is a diagram showing two springs in series representative of a chest in series with a non-rigid surface.
Figure 19:
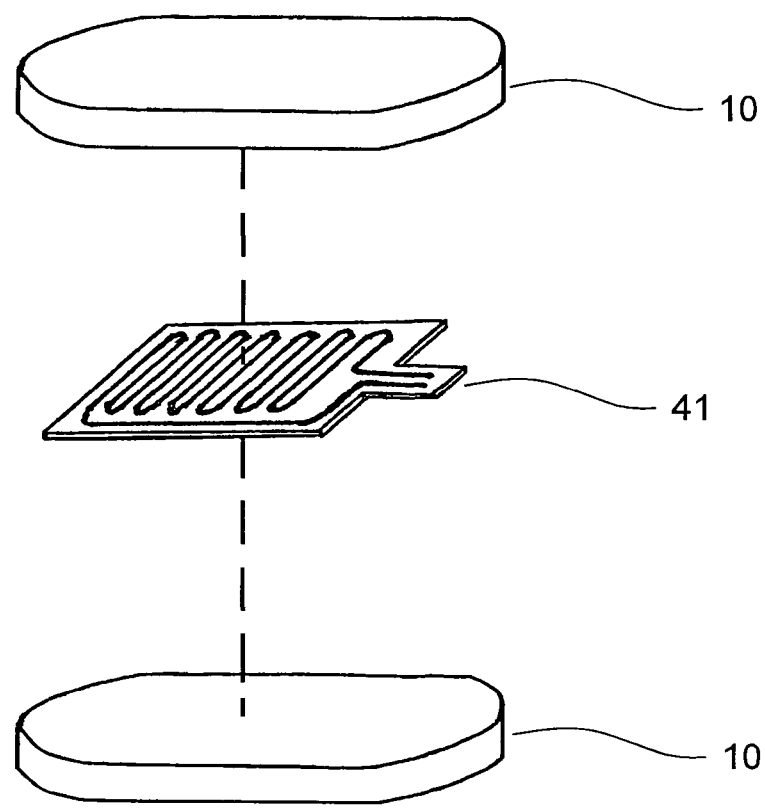
FIG. 19 is a diagram showing an example compression unit having a force sensor.
Figure 20:
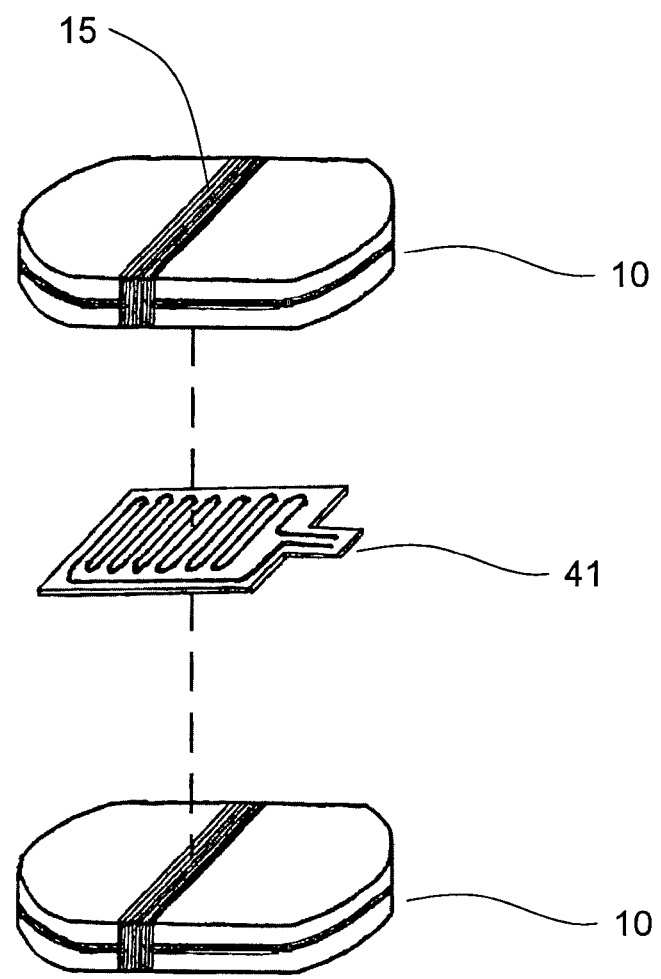
FIG. 20 is a diagram showing an example compression unit having a force sensor.

Reference is now made to FIG. 18. In this example, the processor may be configured to model the patient's chest and the surface as series springs using force measurements and translational data derived from the force and motion or position sensors, respectively. For example, force measurement data from the reference component in the surface unit 9 may be used to calculate the spring constant of the surface 7 using Hooke's law. For example, it is known that $F_b=k_b x_b$, where the force measured by the reference component, $F_b$, causes a downward translation of the surface 7, $x_b$, as measured by the motion or position sensor in the surface unit 9. The spring constant for the surface 7 may be calculated by rearranging the above equation to solve for $k_b$: $k_b=F_b/x_b$. It is also known that $F_t=k_t x_t$, where the force measured by the signal component, $F_t$, causes a downward translation of the patient's chest 11 and the surface 7, collectively termed $x_t$, as sensed by the motion or position sensor in the compression unit 10. This may be modelled as a series combination of a chest spring 37 representing chest compliance and a surface spring 38 representing surface compliance. The two springs are sandwiched between the CPR administrator's hands 39 and the base 40 or floor supporting the surface 7. Therefore, the force applied by the CPR administrator to the patient's chest 11, $F_t$, is also the force acting on the surface 7 directly below the patient's chest 11. If the surface unit 9 is not positioned directly below the point of compression 32, the force sensed by the reference component, $F_b$, is less than the total force applied to the patient's chest 11, $F_t$. However, since $k_b$ is now known, $F_t$ may be substituted into the original equation for the surface unit 9 to solve for $x_m$, the translation of the surface 7 directly below the point of compression: $x_m=F_t/k_b$. This translational movement, $x_m$ may be subtracted from the movement sensed by the signal component, $x_1$, to estimate the depth of the compression. The translational movements ($x_t$ and $x_b$) may be sensed by any suitable motion or position sensor, for example an accelerometer, a velocity sensor, or any other suitable motion sensor. Alternatively, the translational displacement may be sensed using position sensors, such as a field generator and a field detector, as described above. In the example shown in FIG. 19, the force sensor 41 may be sandwiched into a compression unit 10 housing another sensor (e.g., an accelerometer). In the example shown in FIG. 20, the force sensor 41 may be sandwiched into a compression unit 10 housing a field detector 15.

Figure 21:
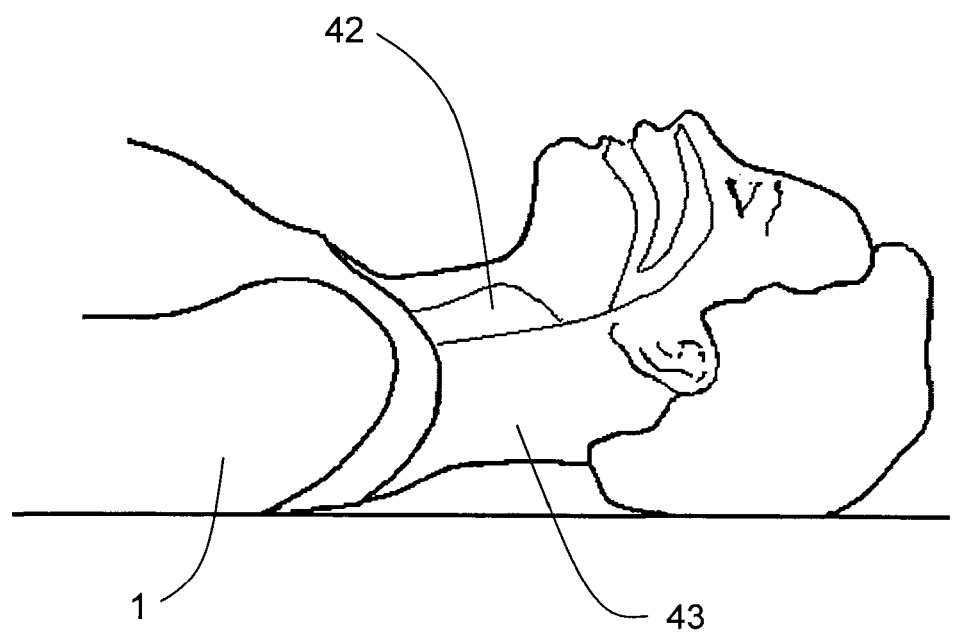
FIG. 21 is a side view of a patient's airway in the absence of a neck support.
Figure 22:
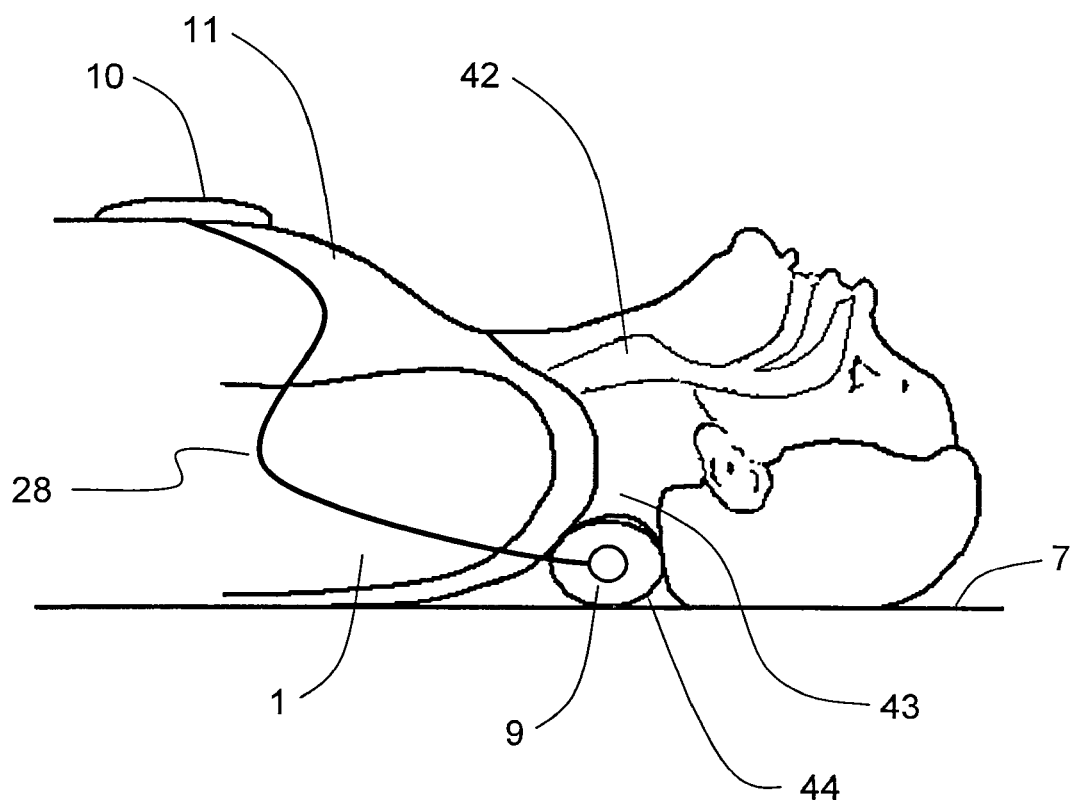
FIG. 22 is a side view of a patient's airway when an example neck support is used.
Figure 23:
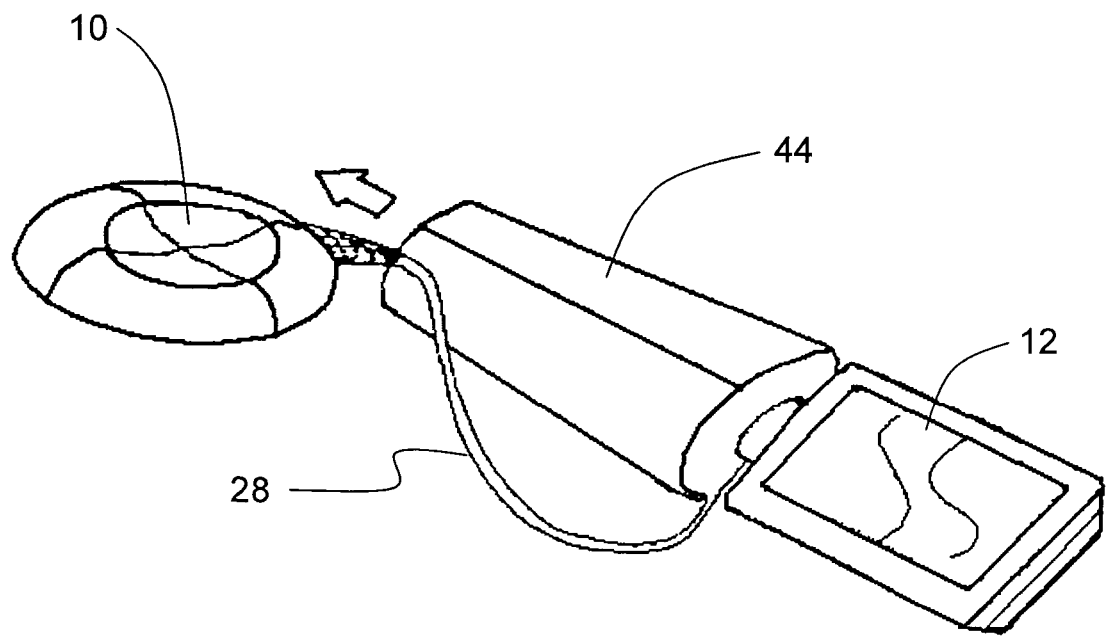
FIG. 23 is an illustration of an example neck support embodiment of the present disclosure.

In some example embodiments, the surface unit 9 is adapted to be positioned outside of the reduced-flex zone 34. Reference is now made to FIGS. 22 and 23. In some examples, the surface unit 9 may be positioned under the neck of the patient 1, for example it may be provided in a neck support. When a patient 1 is lying flat on a surface 7, the patient's airway 42 may not be completely open, as shown in FIG. 21. By propping the neck 43 up and back, for example with a neck support 44, the airway 42 may be fully opened to improve transfer of oxygen into the lungs as shown in FIG. 22. A neck support 44 may be particularly useful when the patient 1 is on a non-rigid or deformable surface 7. As the surface 7 below the patient 1 moves during a chest compression, the neck 43 of the patient 1 may be forced into a closed airway position. A neck support 44 helps to ensure that the airway 42 remains open during administration of CPR. A surface unit 9, for example having a force sensor as the reference component, provided in the neck support 44 may be used to determine a compression parameter. In the example shown in FIG. 23, the neck support 44 may also contain a feedback component 12 (e.g., audio and/or visual feedback component) that provided to the CPR administrator during the resuscitation process. In this example, the compression unit 10 may be connected to the neck support 44 by a physical tether 28 (e.g., a cable), as shown, or the compression unit 10 may communicate using a wireless connection.

Incorporation into a Firm Support

While the aforementioned example embodiments describe the surface unit 9 as being placed beneath the back, shoulder or neck of the patient 1, other example embodiments may have the surface unit 9 attached to or provided in a relatively firm support that is positioned between the patient's back and the surface 7 (e.g., a non-rigid surface). The firm support may allow for a more efficient transfer of force to the patient's chest 11 during CPR. The firm support between the patient's back and the surface 7 may decrease the amount of movement of the surface 7. When the firm support is placed beneath the patient 1, the force applied to the patient's chest is not primarily absorbed by the non-rigid surface 7 below. The firm support may be a cardioboard, a stretcher, backboard, or any other suitably firm, flat object. A cardioboard is a common tool used in hospitals to increase the effectiveness of CPR. It is typically a small board that may be placed behind the back of the patient 1 and directly under the point of compression 32.

The surface unit 9 may be attached, clipped, or otherwise provided on the firm support in any suitable position or location since the firm support will move in accordance with the surface 7. This may help to reduce or eliminate the need for a more accurate placement of the surface unit 9 behind the patient's back. In some examples, the surface unit 9 does not have to be positioned directly behind the patient 1 when it is attached to the firm support provided beneath the patient. Since the support follows the motion and/or displacement of the surface 7 and the surface unit 9 is on and therefore follows the motion and/or displacement of the support, the motion and/or displacement of the surface unit 9 is in accordance with that of the surface 7. Thus, the motion and/or displacement of the surface 7 may be taken into account in determination of a compression parameter, as described above. In other examples, the surface unit 9 and the compression unit 10 may be each provided in a block or wedge or provided in the electrode pads of an external defibrillator.

Figure 24:
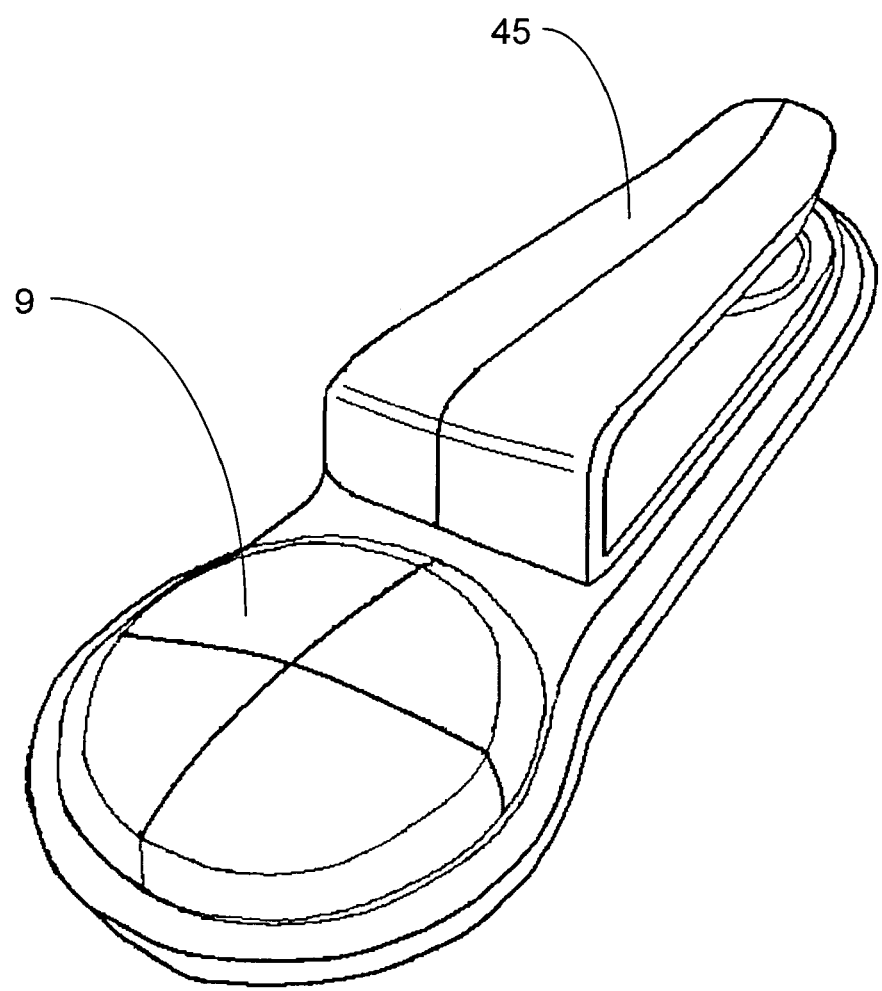
FIG. 24 is an illustration of an example of the surface unit with an attachment mechanism.
Figure 25:
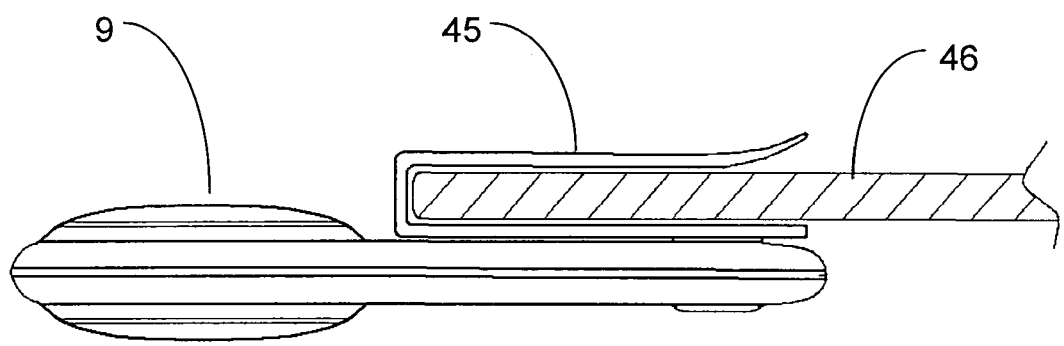
FIG. 25 is a side view of an example of the surface unit attached to a cardioboard or other relatively rigid support.

Reference is now made to FIGS. 24 and 25. In certain embodiments, the surface unit 9 may include an attachment mechanism, such as a clipping mechanism 45, for example to attach the surface unit 9 to a firm support, such as a cardioboard 46. The clipping mechanism 45 may slide over the edge of the cardioboard 46, thus holding the surface unit 9 stationary with respect to the cardioboard 46, for example as shown in FIG. 25. In this configuration, the surface unit 9 does not have to be placed directly behind the patient, as it is attached to the firm support (e.g. the cardioboard 46) that is beneath the patient.

Figure 26:
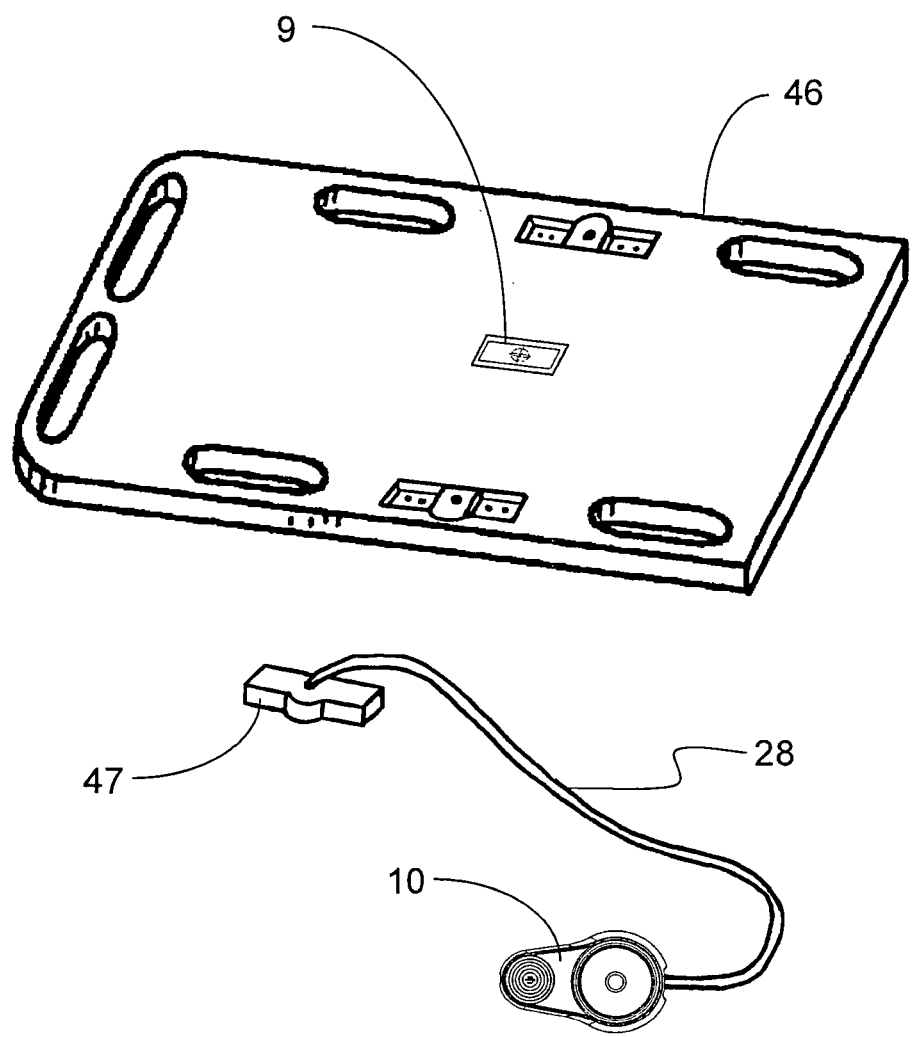
FIG. 26 is an illustration of an example surface unit provided in a cardioboard and a compression unit that may be attached to the cardioboard.
Figure 27:
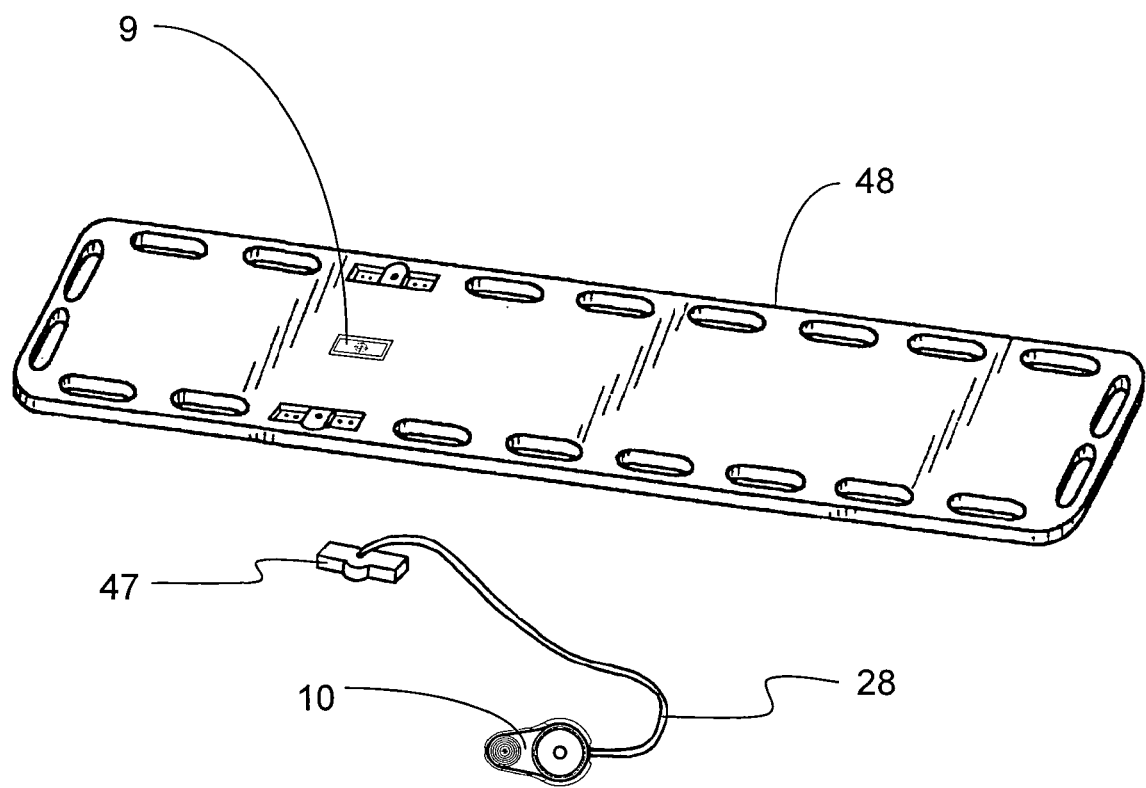
FIG. 27 is an illustration of an example surface unit provided in a backboard and a compression unit that may be attached to the backboard.
Figure 28:
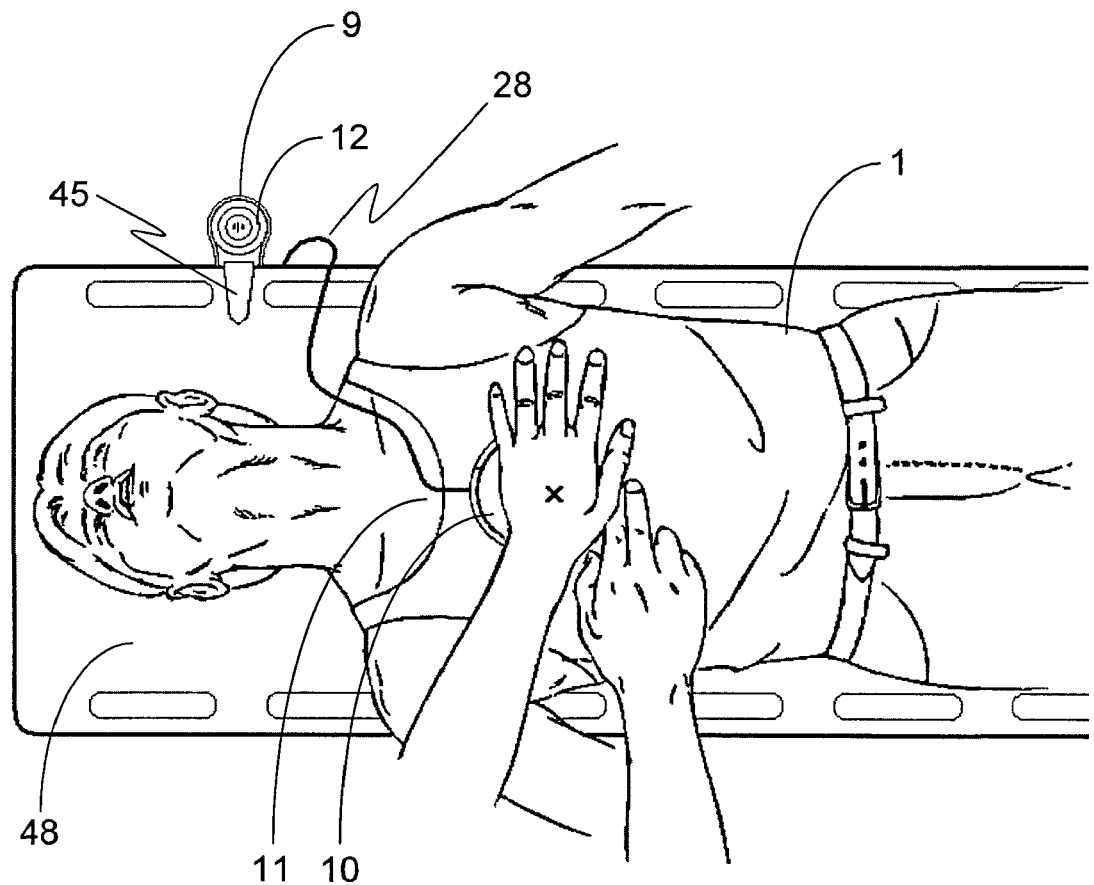
FIG. 28 is a top view of a patient on a backboard with an example surface unit attached to the side of the backboard.

Reference is now made to FIG. 26. In some examples, the surface unit 9 may be embedded or inserted directly into the cardioboard 46. The compression unit 10 may be attachable to the cardioboard 46, for example with a connector 47, to allow data and power to be transferred to and from the surface unit 9. In some examples, the surface unit 9 may be incorporated directly into a backboard 48, stretcher, gurney or any other suitable support and the compression unit 10 may be attachable to the backboard 48, stretcher, gurney or support, for example using a connector 47 as shown in FIG. 27. In some examples, the surface unit 9 may also be attached onto a stretcher or backboard 48 using the clipping mechanism 45 previously described as shown in FIG. 28. When clipped onto the side of a backboard, cardioboard or other firm support, the surface unit 9 may not be directly under the patient 1 and may be at least partially visible to the CPR administrator. As such, the surface unit 9 may include a feedback component 12 for providing visual feedback to the CPR administrator, for example on a portion of the surface unit 9 that extends beyond or above the board it is attached to.

Figure 29:
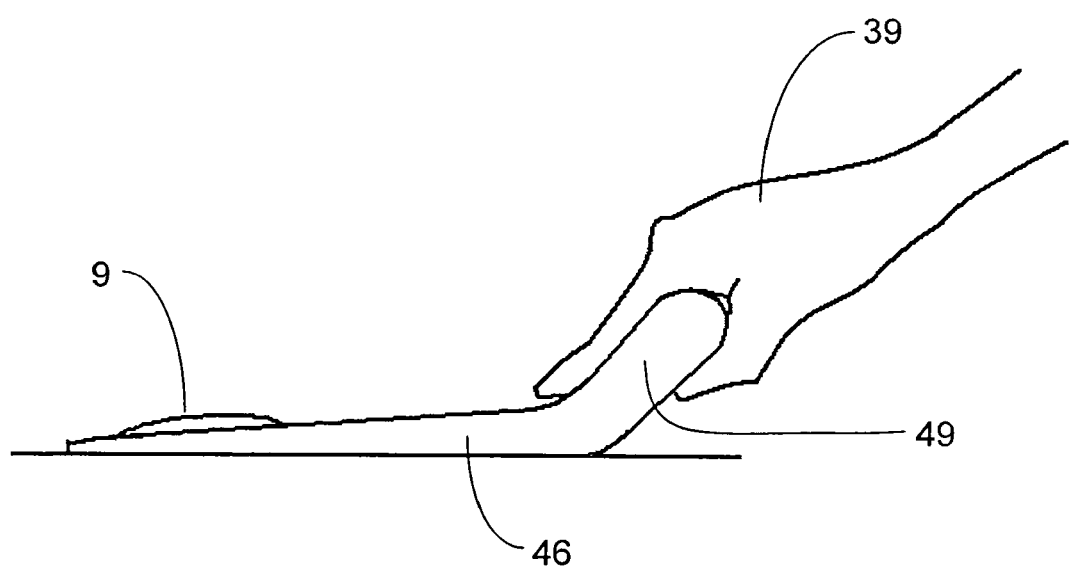
FIG. 29 is a side view of an example surface unit inside a board with a handle.
Figure 30:
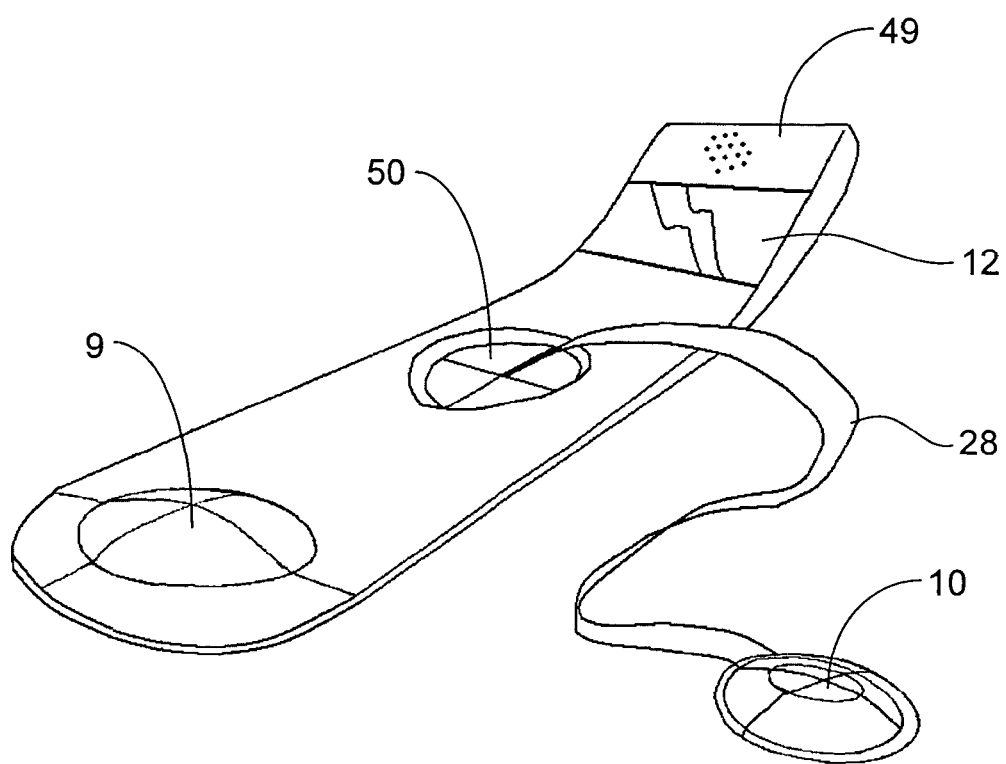
FIG. 30 is an illustration of an example surface unit provided in a backboard with a handle and an example compression unit attached.

Reference is now made to FIG. 29. In some examples, a cardioboard 46, backboard or other suitable firm support may be designed so that it is relatively easily slid between the patient 1 and the surface 7. In the example shown, the surface unit 9 may be provided in the cardioboard 46, and the cardioboard 46 has an extension 49 that may be relatively easily grasped by the hands of the CPR administrator 39. Such an extension 49 may provide additional leverage to the CPR administrator when pushing the cardioboard 46 beneath the patient 1. A feedback component 12 may also be provided in the cardioboard 46, for example in the extension 49, as shown in FIG. 30. In the example shown, the compression unit 10 may be stored in a compartment 50 within the cardioboard 46 and may be detachable or removable for use.

Incorporation into Surface

In some examples, the surface unit 9 may be incorporated into the surface 7 (e.g., a non-rigid surface) beneath the patient 1. For example, the surface unit 9 may be embedded into a mattress or may be sewn onto the mattress textile. In some examples, a surface unit 9 (e.g., having a flexible pressure sensor as the reference component) may be firmly adhered to the outer surface of the mattress. When the patient 1 is placed on the mattress, the surface unit 9 will already be in position under the patient's back. A compression unit 10 may attach to the mattress containing the surface unit 9 and may be positioned on the chest 11 of the patient 1. Due to the surface unit 9 being attached to the mattress, the motion and/or displacement of the surface will be taken into account for determination of compression parameters.

Figure 31:
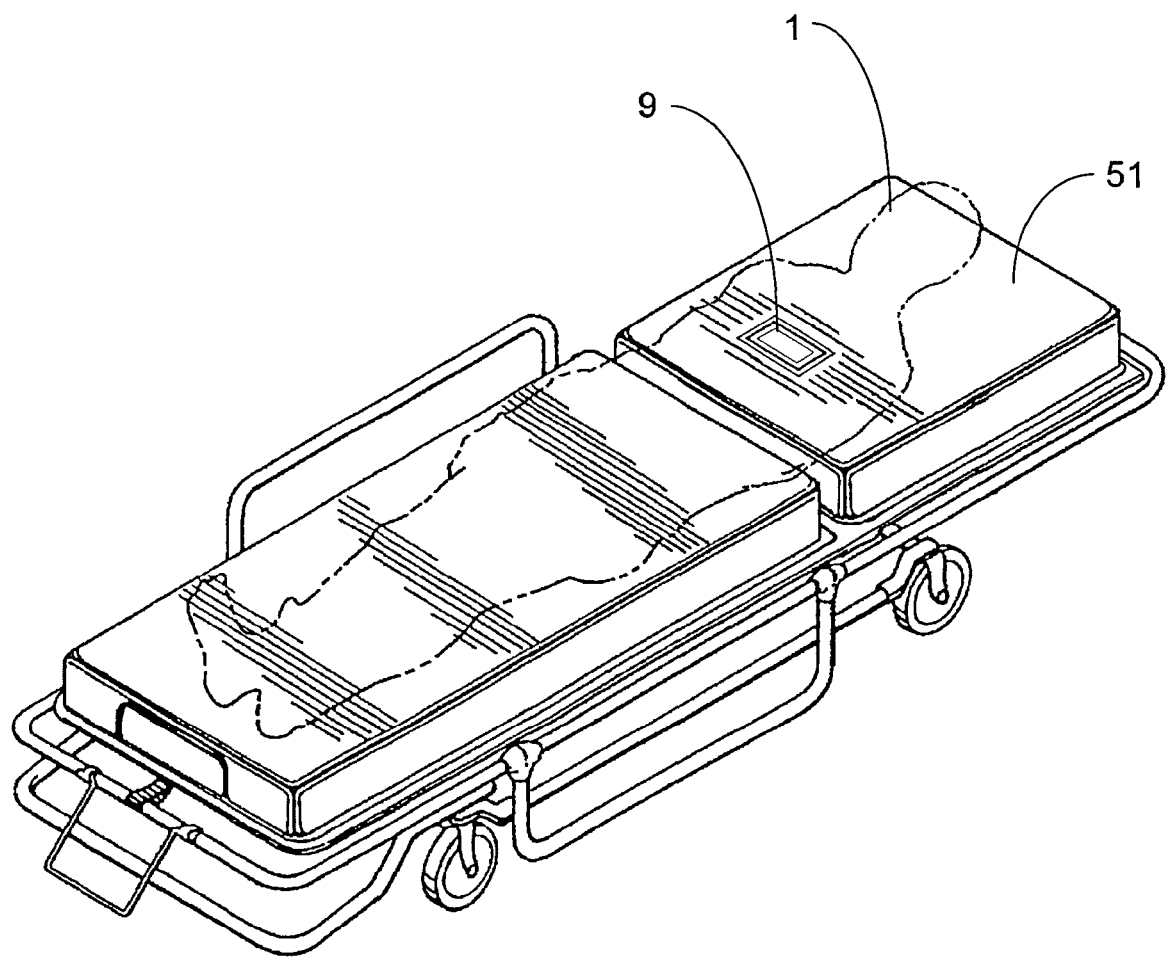
FIG. 31 is an illustration of an example surface unit provided in a hospital bed.

Reference is now made to FIG. 31. In some examples, the surface unit 9 may be directly incorporated into the surface 7. In the example shown, the surface unit 9 may be provided in a non-rigid surface such as a mattress 51 (e.g., by directly adhering the surface unit 9 to the mattress 51) or may be otherwise incorporated into the textile of the mattress 51. For example, a surface unit 9 having a pressure sensor as the reference component may be adhered to the outer surface of the mattress 51 so that when the patient is placed on the surface of the mattress 51, the surface unit 9 may already be properly positioned to move in accordance with the surface beneath the patient (in this example, the surface of the mattress 51). The compression unit 10 may be attached to the surface 7 and may be placed on the chest 11 of the patient when administering CPR. In other examples, the reference component may be an accelerometer that may be adhered to the surface of the mattress 51 prior to commencing the resuscitation process. In such an example, the surface unit 9 may be substantially flat and include an adhesive backing on one side. The adhesive backing may be activated and the surface unit 9 may be directly attached to the surface 7. When the patient 1 is placed on the surface 7, the patient 1 will be on top of the already positioned surface unit 9.

Different Body Sizes

Figure 32:
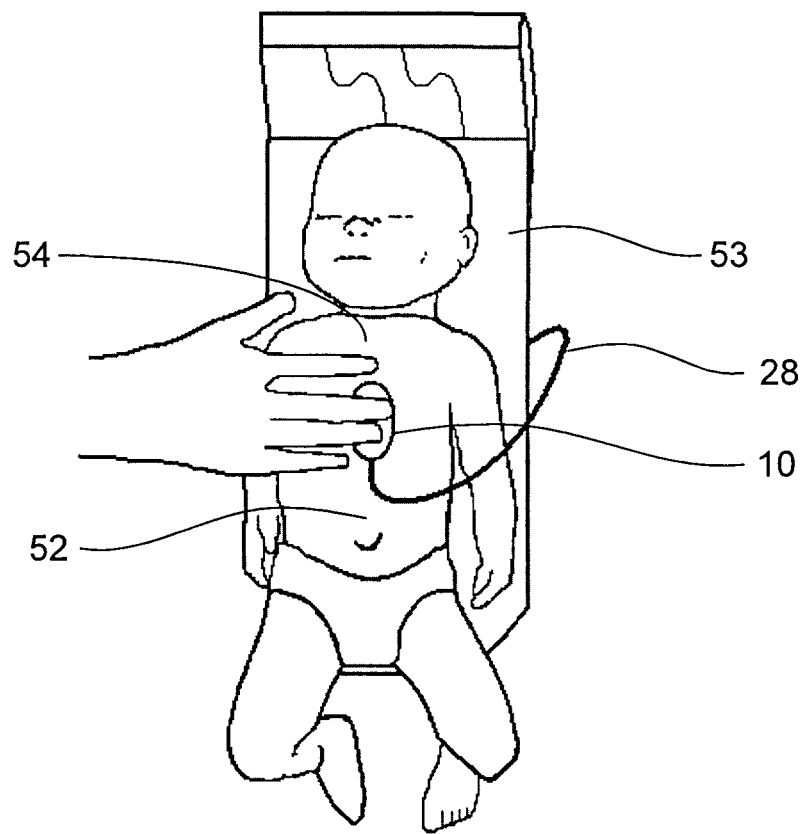
FIG. 32 is a top view of an infant on top of an infant backboard with an example surface unit.

The presently disclosed device may be adaptable to a different patient body types. For example, an infant 52 or small child may be placed on an infant backboard 53 housing a surface unit 9, as shown in FIG. 32. The compression unit 10 may be tethered to the infant backboard 53 and may be placed on the infant's chest 54. The infant backboard 53 may be placed on the surface 7 and CPR may be administered, with the device being used to determine a compression parameter, as described above. Additionally, the present device may determine a suitable compression depth based on an estimated patient's body size.

Current CPR guidelines recommend that the depth of compression on infants and children be adjusted for the depth of the chest cavity. The processor may determine the distance between the surface unit 9 and compression unit 10 and may use this determined distance to determine or estimate the patient's body size and hence a suitable depth of chest compressions. The suitable compression depth may be taken into account in determining the compression parameters, and may be included in feedback provided to the CPR administrator. Such a technique may be suitable for adult patients as well. For example, a large-framed adult with a thick chest may require deeper compressions than an adult with a smaller frame. The determined distance between the compression unit 10 and surface unit 9 may thus be used to determine or estimate the patient's chest height and a suitable compression depth may be determined accordingly.

Incorporation into a Defibrillator

Typically, following cardiac arrest, an external defibrillator may be used to resuscitate the patient. Studies have shown the importance of combining high quality CPR with prompt defibrillation. Since external defibrillators are often used in hospital and emergency settings, it is not uncommon for medical personnel to be working on a patient supported on a non-rigid surface. Proper defibrillation requires the accurate placement of the two separate electrode pads. Typically, the top electrode pad is positioned just below the right shoulder of the patient and the side electrode pad is placed on the left side of the patient, just below the ribcage. In some examples, at least one of the surface unit 9 and the compression unit 10 may be provided in the electrode pad assembly of the defibrillator.

Figure 33:
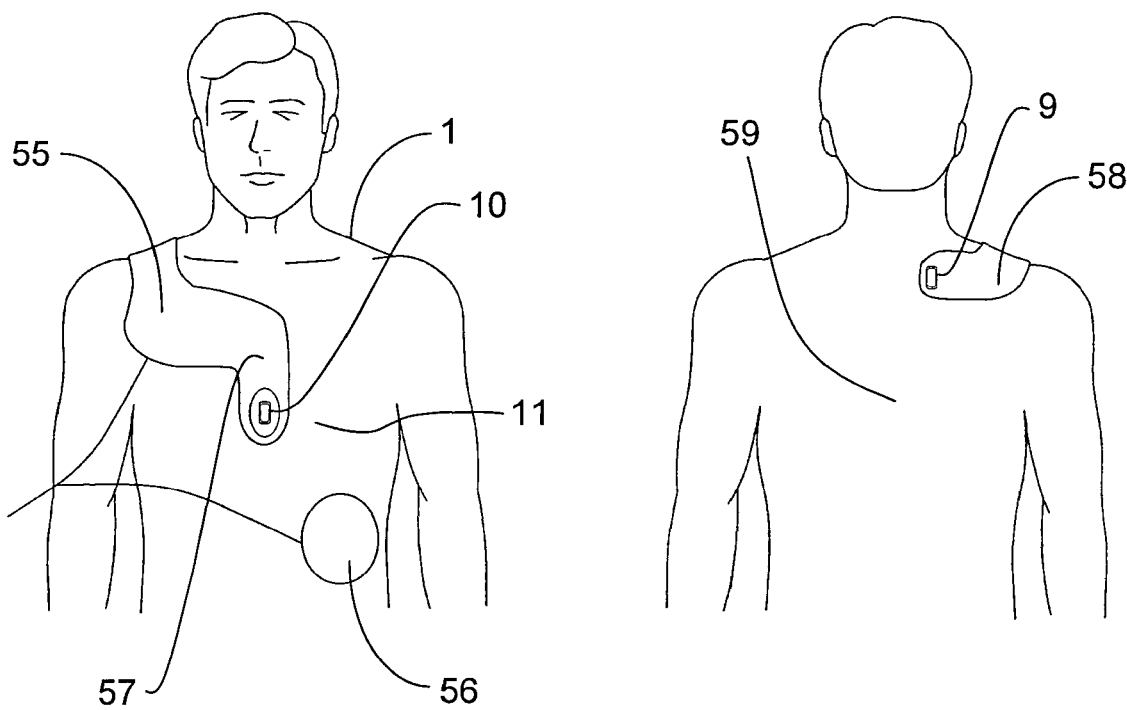
FIG. 33 is an illustration showing an example compression unit and an example surface unit both provided in a defibrillator's top electrode pad.
Figure 34:
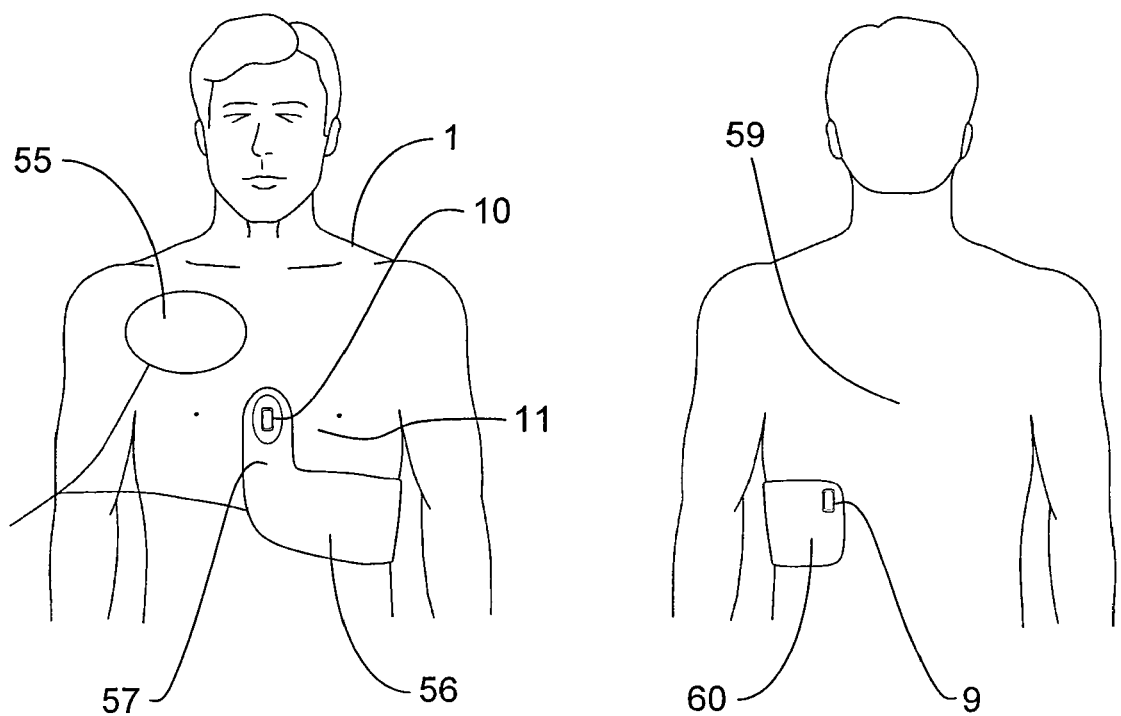
FIG. 34 is an illustration showing an example compression unit and an example surface unit both provided in a defibrillator's side electrode pad.
Figure 35:
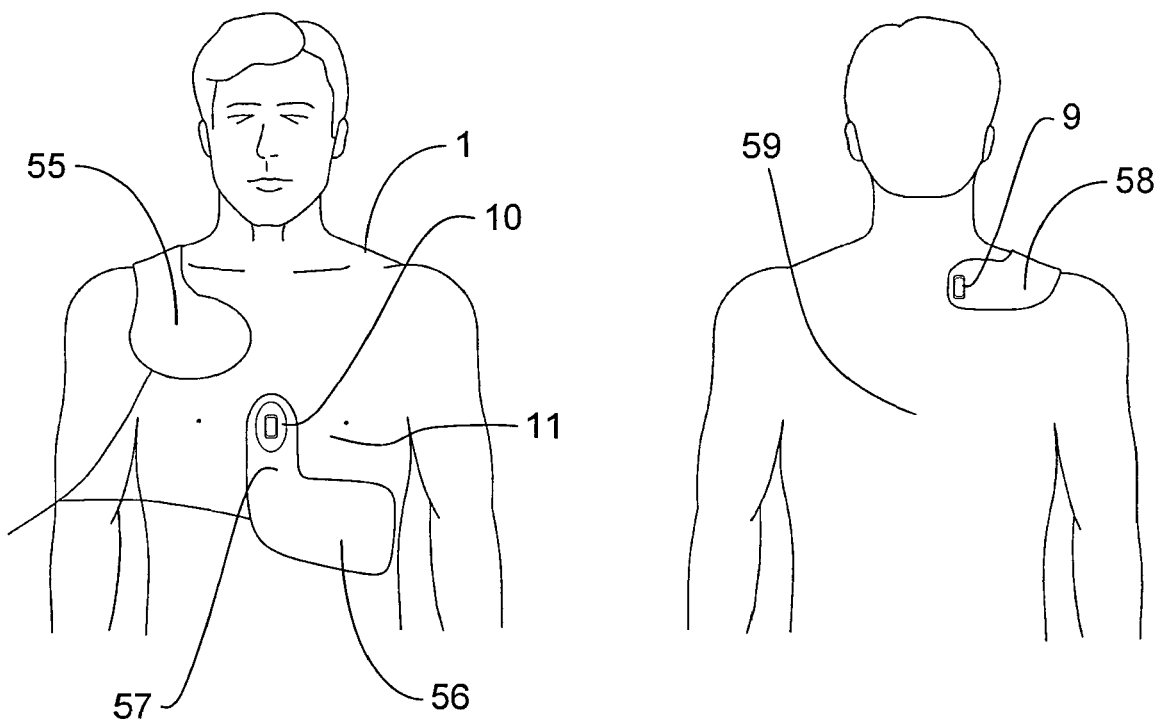
FIG. 35 is an illustration showing an example surface unit provided in a defibrillator's top electrode pad and an example compression unit provided in a defibrillator's side electrode pad.
Figure 36:
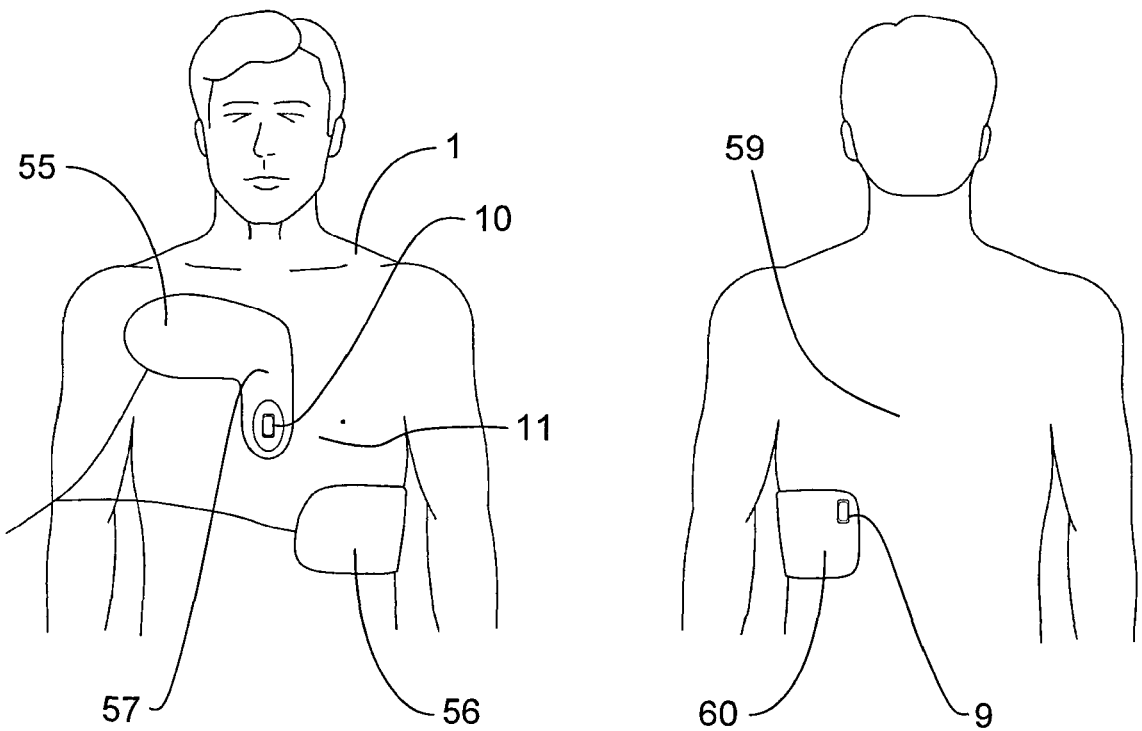
FIG. 36 is an illustration showing an example compression unit provided in a defibrillator's top electrode pad and an example surface unit provided in a defibrillator's side electrode pad.

Reference is now made to FIGS. 33, 34, 35 and 36. The variability of electrode pad size, shape and placement enables a range of different configurations. For example, as shown in FIG. 33, the compression unit 10 and surface unit 9 may both be housed inside the top electrode pad 55, leaving the side electrode 56 free of either unit. The top electrode pad 55 may be configured so that the chest portion 57 of the top electrode pad 55 extends over the chest 11 of the patient 1 and provides the compression unit 10 while the shoulder portion 58 of the top electrode pad 55 extends over the shoulder and behind the back 59 of the patient 1 and provides the surface unit 9. In another example, as shown in FIG. 34, both the compression unit 10 and surface unit 9 may be provided in the side electrode pad 56. The chest portion 57 of the side electrode pad 56 may extend over the chest 11 of the patient 1 and may provide the compression unit 10 while the side portion 60 of the side electrode pad 56 provide the surface unit 9, and may extend out the side of the side electrode pad 56 and wrap around the patient 1 so that the surface unit 9 is positioned the patient's back 59. In another example, as shown in FIG. 35, the surface unit 9 may be provided in the top electrode pad 55 and the compression unit 10 may be provided in the side electrode pad 56. In another example, as shown in FIG. 36, the compression unit 10 may be provided in the top electrode pad 55 and the surface unit 9 may be provided in the side electrode pad 56. Other configurations may be possible.

Figure 37:
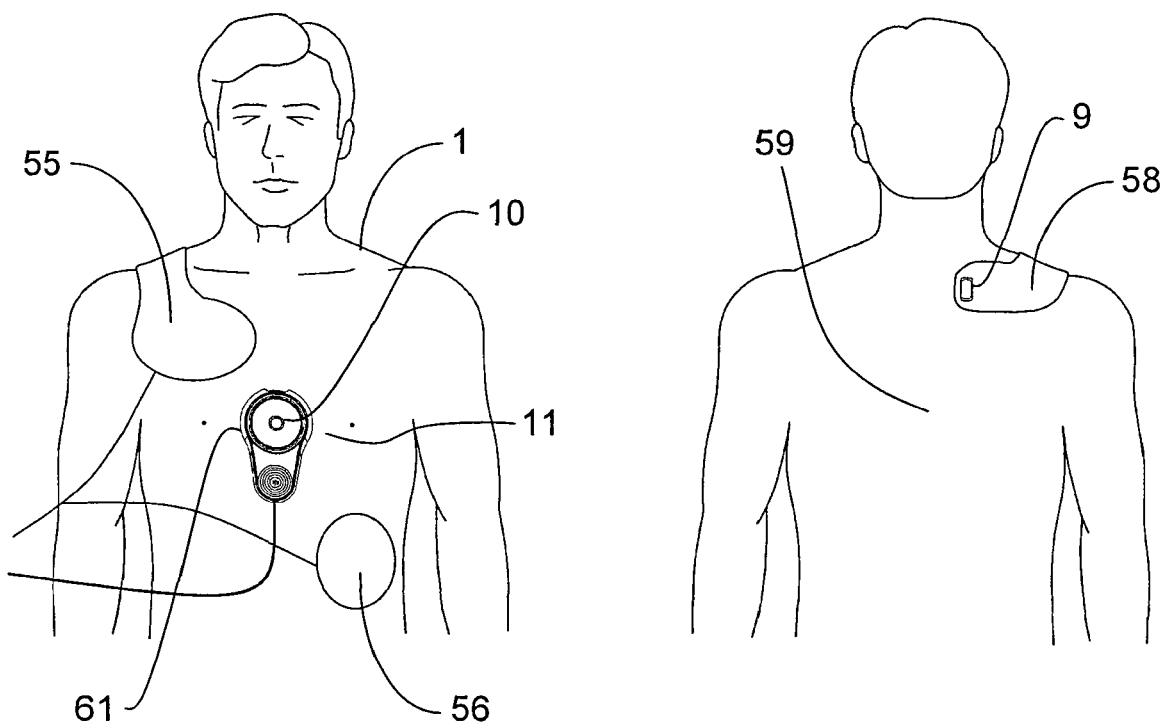
FIG. 37 is an illustration showing an example surface unit provided in a defibrillator's top electrode pad and an example compression unit provided as a separate block on the chest of the patient.
Figure 38:
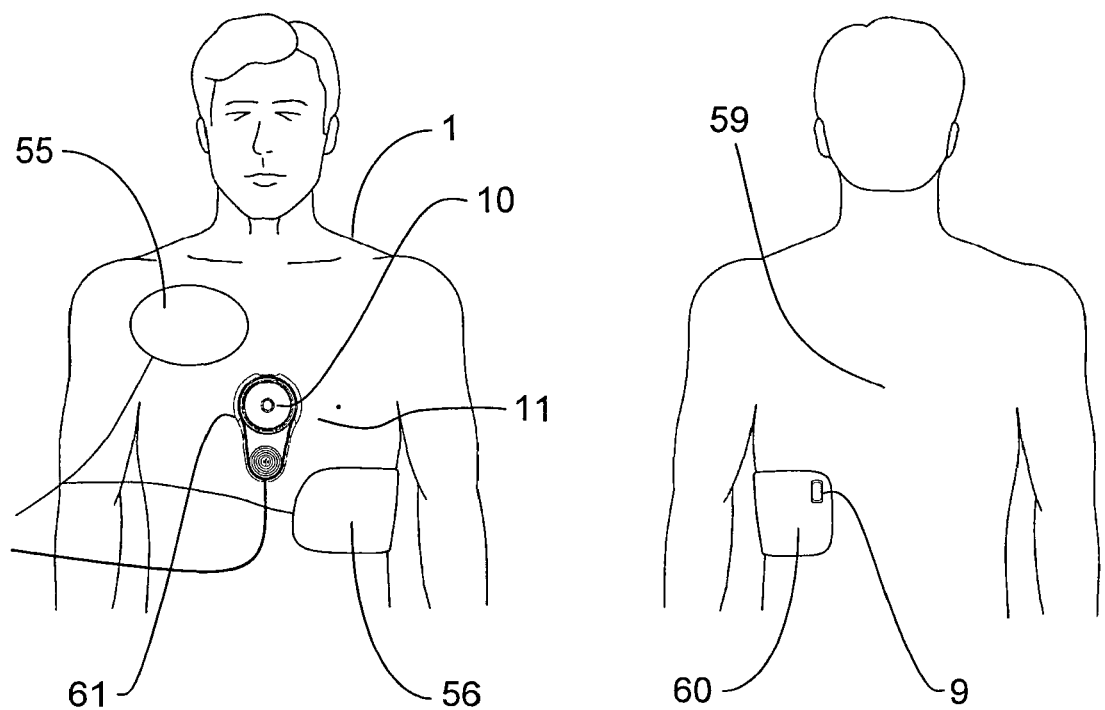
FIG. 38 is an illustration showing an example surface unit provided in a defibrillator's side electrode pad and an example compression unit provided as a separate block on the chest of the patient.

Reference is now made to FIGS. 37 and 38. In some examples, the compression unit 10 may be provided in a separate chest block 61 or pad that is not part of the electrode pad assembly of the defibrillator. In some examples, the surface unit 9 may be provided in either the top electrode pad 55 (as shown in FIG. 37), or the side electrode pad 56 (as shown in FIG. 38) while the compression unit 10 is provided in a chest block 61 or pad separate from the electrode pads.

Figure 39:
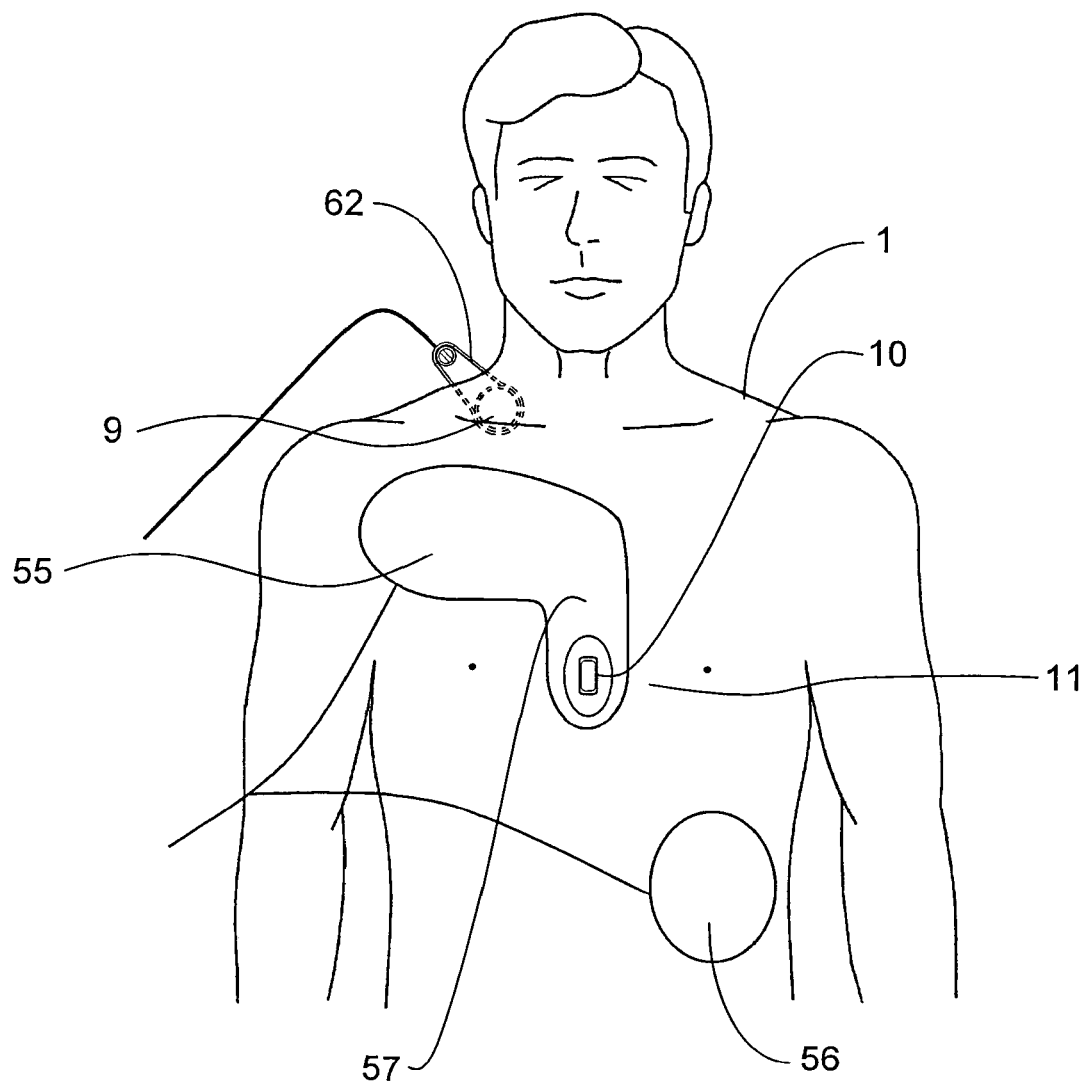
FIG. 39 is an illustration showing an example compression unit provided in the defibrillator's top electrode pad and an example surface unit provided as a separate block behind the back of the patient.
Figure 40:
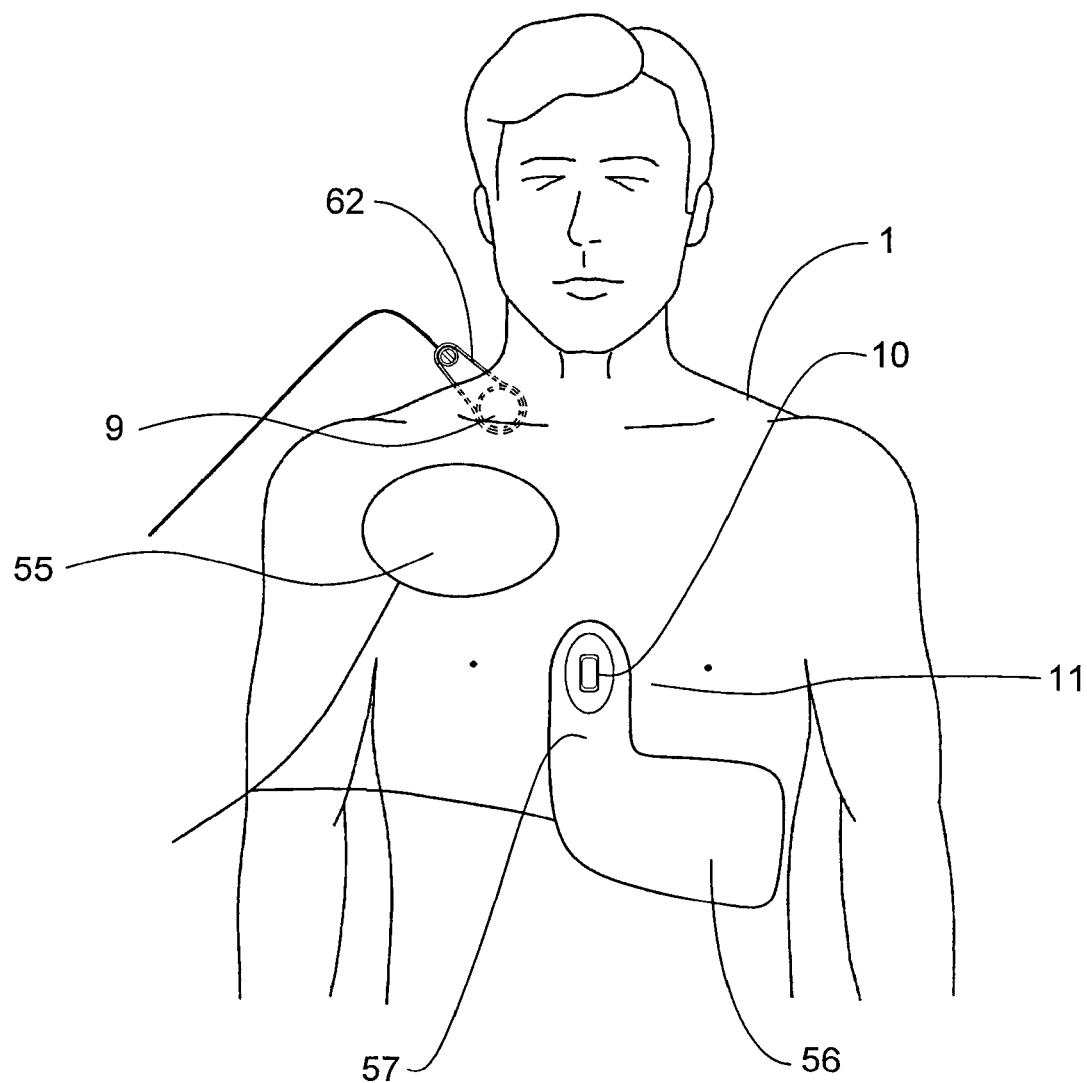
FIG. 40 is an illustration showing an example compression unit provided in the defibrillator's side electrode pad and an example surface unit provided as a separate block behind the back of the patient.

Reference is now made to FIGS. 39 and 40. In some examples the surface unit 9 may be provided in a separate back block 62 or pad separate from the electrode pad assembly of the defibrillator, and the compression unit 10 may be provided in either the top electrode pad 55 (as shown in FIG. 39), or the side electrode pad 56 (as shown in FIG. 40).

Figure 41:
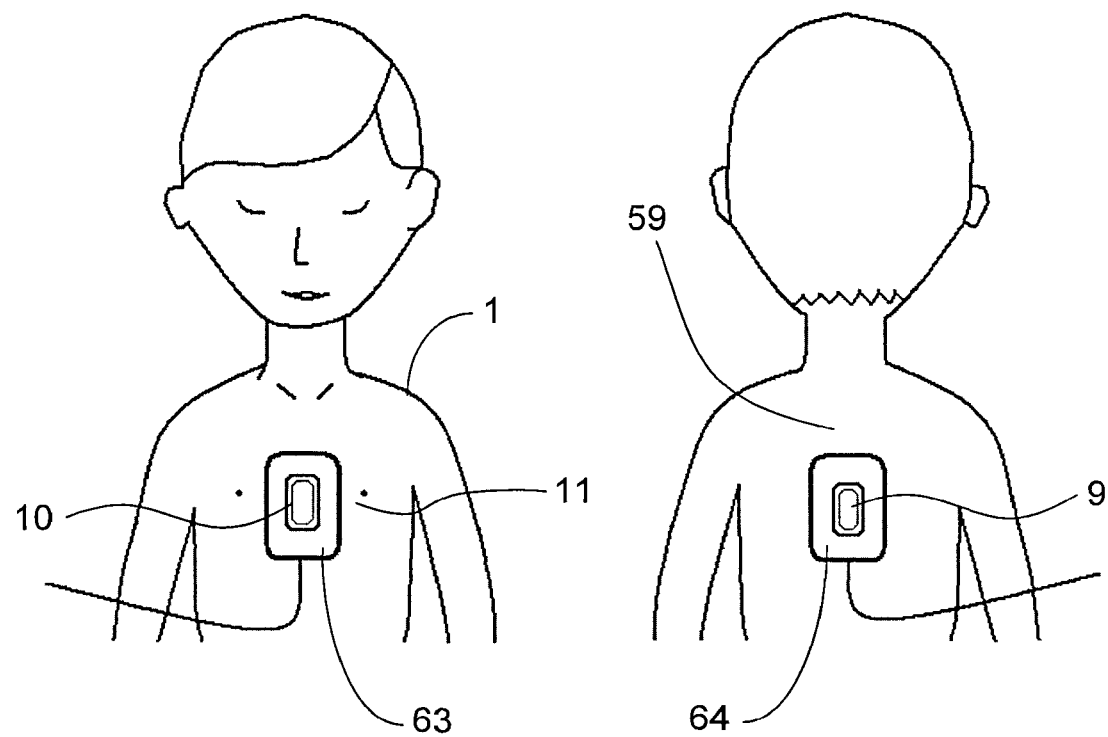
FIG. 41 is an illustration showing an example surface unit provided in a defibrillator's back electrode pad and an example compression unit provided in a defibrillator's front electrode pad.

Reference is now made to FIG. 41. In some situations, external defibrillation requires the use of a front electrode pad 63 and a back electrode pad 64. For example, this configuration is commonly seen in pediatric external defibrillation. To accommodate this configuration, in some examples, the surface unit 9 may be provided in a defibrillator's back electrode pad 64, and the compression unit 10 may be provided in a defibrillator's front electrode pad 63.

Compression Parameters

Although determination of chest compression depth as been described as an example of a compression parameter that may be determined by the presently disclosed device, other compression parameters may also be determined. For example, the presently disclosed device may determine other CPR parameters, such as chest compression rate (e.g., on a non-rigid surface) by determining the number of chest compressions that have occurred in a given unit of time. Typically, surface bounce and movement of a non-rigid surface beneath a patient may complicate determination of chest compression rate where motion or displacement of the surface is not taken into account. An algorithm for determination of chest compression rate may determine the peaks and valleys of a signal in order to identify a compression. When these peaks are detected, a compression count may be incremented. Abnormal movements and bounces, such as those arising due to motion or displacement of a non-rigid surface, may confuse such an algorithm. The presently disclosed device may help to address this by providing a way to take into account motion or displacement of the surface in determination of a compression parameter such as the chest compression rate.

The presently disclosed device may also be used to determine a CPR parameter such as the adequate delivery of rescue breaths to a patient on a non-rigid surface. For example, as a breath or ventilation is delivered to the patient, the patient's chest may rise. The rising of the chest may be detected as motion of the compression unit. Any motion or displacement of the surface will be taken into account based on motion or displacement of the surface unit, as described above. Furthermore, in some examples, the distance between the surface unit and compression unit may be determined, as described above.

This determined distance may be useful for determining or estimating the approximate volume of the chest cavity of the patient. The determined chest rise may then be correlated to the chest cavity volume to determine an approximate ventilation volume.

The present disclosure provides a device and method for the determination of CPR parameters when a patient is being resuscitated on a non-rigid, flexible or pliant surface. Although certain embodiments and examples have been provided in this disclosure, they are for the purpose of illustration only and are not intended to be limiting. A person skilled in the art would understand that variations may be possible. All references mentioned are hereby incorporated by reference in their entirety.

What is claimed is:

1. A system for determining at least one compression parameter during the administration of cardiopulmonary resuscitation (CPR) on a patient, the system comprising:
   a compression unit having a first accelerometer structured to move with a chest of the patient during a chest compression, the compression unit configured to sense a motion of the compression unit and output a first signal indicative of the motion;
   a surface unit having a second accelerometer located within a neck support, adapted to prop the neck up and back, and structured to move with a surface supporting the patient during the chest compression, the surface unit configured to sense a motion of the surface unit as the surface supporting the patient is displaced during the chest compression and output a second signal indicative of a displacement of the surface caused at least in part by the chest compression; and
   a processor configured to receive the first signal from the compression unit and the second signal from the surface unit, to determine a relative displacement between the compression unit and the surface unit based on the first signal and the second signal, and to determine the at least one compression parameter based on the relative displacement;
   wherein at least one of the compression unit and the surface unit comprises a feedback component for providing feedback to help coach a CPR administrator during the administration of CPR based on the at least one compression parameter.

2. The system of claim 1, wherein the processor is configured to determine the relative displacement by:
   determining a first displacement measurement of the compression unit by converting the first signal to a first velocity measurement and converting the first velocity measurement to the first displacement measurement;
   determining a second displacement measurement of the surface unit by converting the second signal to a second velocity measurement and converting the second velocity measurement to the second displacement measurement; and
   subtracting the second displacement measurement from the first displacement measurement.

3. The system of claim 1, wherein the feedback includes a depth of compression.

4. The system of claim 1, further comprising a base unit having the feedback component for providing feedback to the CPR administrator based on the at least one compression parameter.

5. The system of claim 1, wherein the compression unit is coupled to a first electrode pad and the surface unit is coupled to a second electrode pad.

6. The system of claim 1 wherein the processor is configured to determine the relative displacement by determining displacements of the surface and the chest and subtracting displacement of the surface from the displacement of the chest.

7. The system of claim 1, wherein the compression unit and the surface unit are coupled to a single electrode pad.

8. The system of claim 1, wherein the surface unit includes a support adapted to slide underneath the patient's back.

9. The system of claim 8, wherein the support comprises a handle for providing leverage to assist in sliding the support underneath the patient.

10. A system for determining at least one compression parameter during the administration of cardiopulmonary resuscitation (CPR) on a patient, the system comprising:
    a compression unit having a first motion sensor structured to move with a chest of the patient during a chest compression, the compression unit configured to sense a motion of the compression unit as both a chest of the patient and a surface supporting the patient are displaced during the chest compression and output a first signal indicative of the motion of the compression unit;
    a surface unit having a second motion sensor structured to be located within a neck support, adapted to prop the neck up and back, and the surface unit configured to sense a motion of the surface unit as the surface is displaced during the chest compression and output a second signal indicative of a displacement of the surface caused at least in part by the chest compression; and
    a processor configured to determine the at least one compression parameter based at least in part on a relative displacement between the compression unit and the surface unit that is determined based on the first signal and the second signal;
    wherein at least one of the compression unit and the surface unit comprises a feedback component for providing feedback to help coach a CPR administrator during the administration of CPR based on the at least one compression parameter.

11. The system of claim 10, wherein the first motion sensor is a first accelerometer and the second motion sensor is a second accelerometer, the processor is configured to determine the relative displacement by:
    determining a first displacement measurement of the compression unit by converting the first signal to a first velocity measurement and converting the first velocity measurement to the first displacement measurement;
    determining a second displacement measurement of the surface unit by converting the second signal to a second velocity measurement and converting the second velocity measurement to the second displacement measurement; and
    subtracting the second displacement measurement from the first displacement measurement.

12. The system of claim 10, wherein the first motion sensor includes a first velocity sensor and the second motion sensor includes a second velocity sensor.

13. The system of claim 10, wherein the feedback includes a depth of compression.

14. The system of claim 10, wherein the compression unit is coupled to a first electrode pad and the surface unit is coupled to a second electrode pad.

15. The system of claim 10, wherein the processor is configured to determine the relative displacement by determining displacements of the surface and the chest and subtracting displacement of the surface from the displacement of the chest.

16. The system of claim 10, wherein the compression unit and the surface unit are coupled to a single electrode pad.

17. The system of claim 10, wherein the surface unit includes a support adapted to slide underneath the patient's back.

18. The system of claim 17, wherein the support comprises a handle for providing leverage to assist in sliding the support underneath the patient.

* * * * *